(12) United States Patent
Zhang et al.

(10) Patent No.: US 10,368,586 B2
(45) Date of Patent: Aug. 6, 2019

(54) SMOKING MACHINE FOR ELECTRONIC CIGARETTE

(71) Applicant: SHANGHAI TOBACCO GROUP CO., LTD., Shanghai (CN)

(72) Inventors: Yichun Zhang, Shanghai (CN); Yi Shen, Shanghai (CN); Saijing Zheng, Shanghai (CN); Jing Yang, Shanghai (CN); Chao Chen, Shanghai (CN); Yihan Gao, Shanghai (CN); Aiqun Zheng, Shanghai (CN)

(73) Assignee: SHANGHAI TOBACCO GROUP CO., LTD., Shanghai (CN)

( * ) Notice: Subject to any disclaimer, the term of this patent is extended or adjusted under 35 U.S.C. 154(b) by 0 days.

(21) Appl. No.: 16/067,106

(22) PCT Filed: Dec. 27, 2016

(86) PCT No.: PCT/CN2016/112391
§ 371 (c)(1),
(2) Date: Jun. 28, 2018

(87) PCT Pub. No.: WO2017/114389
PCT Pub. Date: Jul. 6, 2017

(65) Prior Publication Data
US 2019/0021397 A1   Jan. 24, 2019

(30) Foreign Application Priority Data

Dec. 31, 2015   (CN) .......................... 2015 1 1027728
Dec. 31, 2015   (CN) ..................... 2015 2 1136486 U

(51) Int. Cl.
*G01N 1/02*   (2006.01)
*G01N 1/24*   (2006.01)
(Continued)

(52) U.S. Cl.
CPC ......... *A24F 47/008* (2013.01); *G01M 99/005* (2013.01); *G01N 1/24* (2013.01);
(Continued)

(58) Field of Classification Search
CPC .. A24F 47/008; A24F 47/002; G01M 99/005; G01N 1/24; G01N 2001/028; G01N 5/00
See application file for complete search history.

(56) References Cited

U.S. PATENT DOCUMENTS 3,586,007 A * 6/1971 Kelley ................. A24C 5/3406
131/330
3,618,365 A * 11/1971 McArthur ................ A24C 5/34
73/45.1
(Continued)

FOREIGN PATENT DOCUMENTS

CN   103674761 A   3/2014
CN   204203193 U   3/2015
(Continued)

*Primary Examiner* — Jonathan M Dunlap
(74) *Attorney, Agent, or Firm* — Global IP Services; Tianhua Gu

(57) ABSTRACT

The present invention provides a smoking machine for an electronic cigarette, relating to the technical field of electronic cigarettes. The smoking machine for an electronic cigarette comprises: a housing; a rotary disc installed on a side surface of the housing, a central axis of the rotary disc is parallel to a horizontal plane, and the rotary disc rotates relative to the housing with the central axis of the rotary disc as a center, a disc-body smoking through hole is provided on an end face of the rotary disc, a housing sealing member is disposed on a side surface of the housing, a sealing ventilation hole penetrating into the housing in a horizontal direction is provided in the housing sealing member, and an end face of the housing sealing member is in contact with the end face of the rotary disc; and a main control circuit board electrically connected to the rotary disc. The rotary disc of
(Continued)

the present invention is perpendicular to a horizontal plane, and the electronic cigarette circumferentially rotates along with the rotary disc in a smoking experiment process, so that tobacco tar in a cigarette cartridge flows and fully immerses the oil guiding cotton, thus ensuring sufficient and steady supply of the tobacco tar to an atomizer, and guaranteeing atomization efficiency, atomization amount, and the stability and accuracy of experiment data.

12 Claims, 18 Drawing Sheets

(51) Int. Cl.
  *G01N 5/00*  (2006.01)
  *A24F 47/00*  (2006.01)
  *G01M 99/00*  (2011.01)
(52) U.S. Cl.
  CPC .............. *G01N 5/00* (2013.01); *A24F 47/002* (2013.01); *G01N 2001/028* (2013.01)

(56) References Cited

U.S. PATENT DOCUMENTS

| | | | | |
|---|---|---|---|---|
| 9,970,871 B2* | 5/2018 | Slurink | ................ | A24C 5/3406 |
| 2017/0241906 A1* | 8/2017 | Slurink | ................ | A24C 5/3406 |

FOREIGN PATENT DOCUMENTS

| | | | |
|---|---|---|---|
| CN | | 205352787 U | 6/2016 |
| CN | | 205352882 U | 6/2016 |
| EP | | 2193727 | 5/2012 |
| WO | WO | 2014206934 | 12/2014 |

\* cited by examiner

SMOKING MACHINE FOR ELECTRONIC CIGARETTE

CROSS REFERENCE TO RELATED PATENT APPLICATION

The present application is the US national stage of PCT/CN2016/112391 filed on Dec. 27, 2016, which claims the priorities of the CN201511027728.4 filed on Dec. 31, 2015 and CN201521136486.8 filed on Dec. 31, 2015, which applications are incorporated herein by reference.

BACKGROUND OF THE PRESENT INVENTION

Field of Invention

The present invention relates to the technical field of electronic cigarettes, and in particular to a smoking machine for an electronic cigarette.

Description of Related Arts

An electronic cigarette is a new type of product. Different from a cigarette manufactured by using conventional tobacco and smoked through lighting, currently, main electronic cigarette products atomize tobacco tar through electrical heating and turns aerosol agent, odorous constituents, and nicotine in the tobacco tar into an aerosol state, so as to simulate an effect of cigarette smoke for inhaling by a consumer and the consumer will obtain a satisfactory feeling. Because the electronic cigarette provides a consumption experience similar to that of a cigarette, and has extremely few harmful ingredients therein relative to the conventional tobacco, the electronic cigarette has become a representative developing direction of a new type of tobacco product. China is a cradle and a main manufacturing site of the electronic cigarette. Globally, 90% or more than 90% of electronic cigarettes are produced in China. However, research and supervision for the electronic cigarette is still in infancy both home and abroad. Currently, a smoking method applied to electronic cigarette detection work and a related technical standard are also in a research and stipulation stage. With continuous development of the product scale, continuous in-depth research, and continuous increased technical requirements, a dedicated instrument device suitable for electronic cigarette detection, especially a smoking machine with perfect functions and stable performance required for product research and development and quality control is more urgently needed.

As shown in FIG. 1, an existing rotary-disc smoking machine has a rotary disc 81 that horizontally rotates. The rotary disc 81 is perpendicular to a horizontal plane with a rotary axis 84 as a central line. Several cigarette clamps are evenly arranged on the rotary disc 81 along a periphery of the rotary disc 81. During smoking, a cigarette is inserted into a cigarette clamp 82, and the rotary disc 81 horizontally rotates. An axial central line of the cigarette is perpendicular to the rotary axis 84. During smoking, smoke is transmitted to a catcher in the rotary-disc smoking machine from a smoke transmission bending pipe 83 of 90 degrees behind the cigarette clamp 82.

As shown in FIG. 2, on an existing linear smoking machine, several smoking hole channels 85 are linearly arranged. Each smoking hole channel 85 is provided with a cigarette clamp correspondingly. Each smoking hole channel 85 is connected to an independent smoking unit. When several cigarettes are lit together, the cigarettes are synchronously smoked based on a smoking capacity defined by a standard.

The working principle of the existing electronic cigarette is as follows: A control circuit is triggered by a switch manually or through pneumatic pressure and supplies power to a heating wire. A current enables the heating wire to generate a high temperature. A fiberglass oil guiding rope twisting inside the heating wire is affected by the high temperature and generates a wick effect. Tobacco tar is continuously transmitted to a high temperature end along the fiberglass oil guiding rope. When reaching a twisted position of the heating wire, the tobacco tar is instantly heated and vaporized into smoke. A smoker smokes by using a cigarette holder. Airflow enters from a vapor inlet hole, and vapor smoke generated in an atomization cavity is inhaled from the cigarette holder to obtain a feeling similar to cigarette smoking. Because of a gravity relationship, the tobacco tar can flow in a storage cavity but is unevenly distributed. The electronic cigarette does not move on the existing linear smoking machine, but on the existing rotary-disc smoking machine, the electronic cigarette horizontally rotates. The tobacco tar is always deposited at a lower portion of a liquid storage cavity due to the gravity. The tobacco tar is consumed in a continuous test process. When a remaining amount of the tobacco tar cannot ensure that the upper fiberglass oil guiding rope is always immersed and replenished by the tobacco tar, a great change may occur on atomization amount due to insufficient tobacco tar replenishment amount, and a smoke amount is decreased. For different electronic cigarette sample rooms or individual rooms having same design, different atomization results may be generated in an actual detection process. Compared with some electronic cigarette oil storage cavities having different types of design, for example, an electronic cigarette whose oil guiding cotton is wrapped in oil storage cotton, the tobacco tar replenishment amount and timeliness of replenishment cause a difference due to different detection devices or methods. Finally, a deviation and a larger error of a detection result are caused.

Both of mechanisms of the two conventional smoking machines are not provided with a manually or linkage controlled pressing part, and do not have a function for testing a manually triggered electronic cigarette.

For automatic determination of smoking termination of a conventional cigarette, that is, position determination when the cigarette is completely burned, the two smoking machines use a method in which a cotton thread in close contact with the cigarette is burned away or an infrared sensing identification manner. An electronic cigarette has no lighting or extinguishment process, the smoking machine cannot directly judge online whether tobacco tar or a battery quantity of the electronic cigarette runs out, that is, a service life of the electronic cigarette.

A cigarette cartridge portion of an electronic cigarette has a large tobacco tar storage capacity. A total aerosol releasing quantity after atomization far exceeds a catching capability of a single fiberglass Cambridge filter. Therefore, when quality stability performance of the electronic cigarette during continuous use is continuously tested, a filter catcher must be changed after several puffs are smoked. In addition, in consideration of a real-time monitored changing condition of the aerosol releasing quantity, multiple catcher weighing actions may be added during catching of a single filter. In use of a conventional smoking machine, an experiment process needs to be manually interrupted to change a catcher provided with a Cambridge filter. In this way, labor costs are inevitably increased, working efficiency is reduced, and a possibility of a deviation or error of an experiment result is increased to a great extent.

SUMMARY OF THE PRESENT INVENTION

In view of the shortcomings in the prior art described above, a smoking machine for an electronic cigarette provided in the present invention resolves the following technical problems:

1. During test, flowing of tobacco tar is automatically implemented by circumferentially rotating an electronic cigarette, so that tobacco tar fully immerses fiberglass tar guiding rope, thereby ensuring a tar guiding effect and atomization amount stability.

2. Through an automatic loading and weighing system of a catcher disposed on the smoking machine for an electronic cigarette. In a smoking gap of the electronic cigarette, a catcher is automatically weighed, and whether smoke is still released is judged based on a variation between two weighing values, that is, a service life of the electronic cigarette is judged. At the same time, the stability of the quality of the electronic cigarette is judged based on several recorded weighing results.

3. Through an automatic loading and weighing system of a catcher disposed on the smoking machine for an electronic cigarette, a new catcher is automatically exchanged in a smoking gap of the electronic cigarette according to a set quantity of smoking puffs or cigarettes. While a test process is not interrupted, a problem that a releasing amount of electronic cigarette smoke exceeds a bearing capability of a filter of a single catcher is resolved.

4. Through an electronic cigarette triggering system and an electronic cigarette rod used in combination, which are carried in the smoking machine for an electronic cigarette, online smoking synchronization triggering can be implemented for a manually triggered electronic cigarette, and external power supply may be performed on a cigarette cartridge of a split-type electronic cigarette by using the electronic cigarette rod used in combination. This resolves a condition in which a battery of the split-type electronic cigarette is in lack of electricity or unstably supplies power, and ensures continuity of the test process.

The present invention provides a smoking machine for an electronic cigarette, comprising: a housing; a rotary disc installed on the housing, the rotary disc rotates relative to the housing with a central axis of the rotary disc as a center; at least one disc-body smoking through hole is provided on an end face of the rotary disc; a housing sealing member is disposed on the housing, a sealing ventilation hole penetrating into an inner portion of the housing is provided in the housing sealing member, and when the sealing ventilation hole is in communication with one end of a catcher, the other end of the catcher is in communication with a smoking apparatus; the central axis of the rotary disc is parallel to a horizontal plane; and at least one cigarette clamping mechanism, comprising a clamping mechanism body and a cigarette clamp disposed on the clamping mechanism body, wherein the cigarette clamp is installed on the disc-body smoking through hole of the rotary disc; one end of the cigarette clamp is a cigarette clamping end for inserting therein an electronic cigarette in a horizontal direction, the cigarette clamp is provided with an axial through hole penetrating in a horizontal direction for smoke to pass through, and the rotary disc is able to rotate to a position to make the axial through hole in communication with the sealing ventilation hole of the housing sealing member.

The central axis of the rotary disc consistent with the present invention is parallel to the horizontal plane, that is, a central line around which the rotary disc rotates is parallel to the horizontal plane. The rotary disc is provided with at least one disc-body smoking through hole. The disc-body smoking through hole passes through two end faces of the rotary disc. The disc-body smoking through hole is provided with the cigarette clamping mechanism for clamping the electronic cigarette. The axial through hole of the cigarette clamp on the cigarette clamping mechanism is disposed in the horizontal direction. When the axial through hole of the cigarette clamp is driven by the rotary disc to rotate to a position aligning with the sealing ventilation hole, the axial through hole comes into communication with the sealing ventilation hole. When the rotary disc rotates for a circle, since the electronic cigarette is clamped and fixed on the cigarette clamping mechanism, and the electronic cigarette rolls for a circle relative to the housing with the central axis of the rotary disc as a center. Tobacco tar stored inside the electronic cigarette flows along an inner wall of a tobacco tar storage cavity for a circle, automatically fully immersing a fiberglass tar guiding rope during flowing. This effectively resolves a smoke output stability problem generated by tobacco tar deposition of a conventional smoking machine, so that a test result is more accurate and close to a real smoking behavior.

At the same time, the catcher is pushed to move in the horizontal direction to a smoking position, so that the catcher is in communication with the sealing ventilation hole of the housing sealing member. That is, during smoking, smoke enters the catcher in the horizontal direction from the axial through hole of the cigarette clamp and the sealing ventilation hole of the housing sealing member. The catcher and the electronic cigarette can be coaxially arranged, which remarkably reduces bumping condensation deposition of aerosol in a bending pipe of a conventional smoking machine, reduces transmission losses, is beneficial to correctness of smoke detection analysis, and resolves a technical problem that is difficult to solve for a conventional smoking machine during smoking of the electronic cigarette.

Preferably, when two or more disc-body smoking through holes exist, the two or more disc-body smoking through holes are evenly arranged on the rotary disc, and distances between central axes of the disc-body smoking through holes and the central axis of the rotary disc are the same. When the rotary disc rotates, this structure enables the axial through hole of the cigarette clamp to sequentially come into communication with the sealing ventilation hole of the housing sealing member.

Further, the housing sealing member is disposed on an upper portion of a side surface of the housing, and a central axis of the sealing ventilation hole and the central axis of the rotary disc both pass through a vertical plane perpendicular to the horizontal plane. The catcher is generally disposed inside from a top portion of the housing. To facilitate the catcher to quickly move to the smoking position corresponding to the sealing ventilation hole of the housing sealing member, the housing sealing member is disposed on an upper portion of the housing, and the central axis of the sealing ventilation hole and the central axis of the rotary disc pass through the vertical plane. This structure enables the axial through hole to move to a position close to the top portion of the housing and come into communication with the sealing ventilation hole of the housing sealing member.

Preferably, an end face of the housing sealing member is in contact with the end face of the rotary disc, and the end face of the rotary disc in contact with the housing sealing member is a plane. This facilitates the end face of the rotary disc and the sealing ventilation hole of the housing sealing member to be sealed during rotation of the rotary disc.

Preferably, the smoking machine for an electronic cigarette further comprises an automatic loading and weighing system of a catcher, and the automatic loading and weighing system of a catcher comprises: a temporary feeding storage store and a temporary discharge storage store, which are disposed on the housing of the smoking machine for an electronic cigarette and in communication with an inner portion of the housing; a transmission mechanism, a balance, an ejector pin assembly, and a discharge transferring mechanism, which are disposed inside the housing; and a main control circuit board electrically connected to the ejector pin assembly, the transmission mechanism, the temporary feeding storage store, the temporary discharge storage store, and the discharge transferring mechanism; the temporary feeding storage store receives the catcher disposed from an outer portion of the smoking machine for an electronic cigarette, and the catcher is taken out from the temporary discharge storage store; a robotic arm is installed on the transmission mechanism, the robotic arm obtains the catcher, the transmission mechanism drives the robotic arm to move, so that the catcher reaches a preparation position and a weighing position, and during moving of the catcher, a central axis of the catcher remains in parallel to a central axis of the sealing ventilation hole; the balance weighs the catcher reaching the weighing position; the ejector pin assembly pushes the catcher to horizontally move to a smoking position, and the ejector pin assembly is provided with a vapor channel for sucking vapor; and the discharge transferring mechanism transfers the catcher to the temporary discharge storage store.

The catcher is disposed inside the temporary feeding storage store from the outer portion of the smoking machine for an electronic cigarette. When the electronic cigarette needs to be smoked, the main control circuit board controls the transmission mechanism to drive the robotic arm to move from the preparation position to a supporting position close to the bottom of the temporary feeding storage store. The preparation position is an initial zero position. The position is a reference position from which the robotic arm moves to other working positions and is used for calculating a moving distance. The main control circuit board controls the catcher in the temporary feeding storage store to fall on the robotic arm. The robotic arm carries the catcher and returns to the preparation position. Subsequently, the main control circuit board controls the ejector pin assembly to push the catcher to the smoking position, so that the catcher comes into connection to a smoking end of the electronic cigarette, and the vapor channel comes into communication with the catcher. The smoking apparatus sucks vapor from the electronic cigarette by using the vapor channel, and vapor smoke of the electronic cigarette is absorbed by the catcher. After smoking is completed, the main control circuit board controls the ejector pin assembly to contract. The main control circuit board controls the transmission mechanism to drive the catcher on the robotic arm to move to the weighing position of the balance and the balance weighs the catcher. When the catcher needs to be taken out, the catcher is transmitted to a discharge position of the temporary discharge storage store by a discharge transferring mechanism.

A ventilation direction of the catcher is always consistent with a smoking experiment direction of the electronic cigarette. The catcher drops material and cooperates with the robotic arm depending on the gravity, thereby ensuring that the catcher is quickly and stably changed within a smoking interval of two puffs. The catcher is always controlled by the robotic arm inside the smoking machine. The smoking position is quite close to the weighing position, so that the robotic arm can quickly move to a required position under control of the main control circuit board. This ensures that the catcher returns to the smoking position after a weighing action is completed within the smoking interval of two puffs.

Further, the discharge transferring mechanism comprises an inclined slideway for the catcher to slide and a discharge pushing cylinder. A horizontal height of an end of the inclined slideway close to the temporary discharge storage store is less than a horizontal height of an end of the inclined slideway far away from the temporary discharge storage store, the discharge pushing cylinder is disposed below the end of the inclined slideway close to the temporary discharge storage store, and a piston rod of the discharge pushing cylinder is located exactly below the temporary discharge storage store.

In order to quickly transfer the catcher to the discharge position, the discharge transferring mechanism is provided with the inclined slideway. After the robotic arm places the catcher at the end of the slideway far away from the temporary discharge storage store, the catcher slides along an inclined direction of the inclined slideway to the end of the inclined slideway close to the temporary discharge storage store. In this case, the piston rod of the discharge pushing cylinder is exactly below the catcher. The main control circuit board controls the piston rod of the discharge pushing cylinder to push the catcher in a vertical direction, so that the catcher can be quickly pushed to the discharge position of the temporary discharge storage store.

Further, the catcher comprises a catching body and a vapor guiding head disposed on each of two axial end faces of the catching body, the robotic arm is formed by two grippers with a V-shaped groove at an end portion, and the V-shaped groove supports the corresponding vapor guiding head. This structure enables the grippers of the robotic arm to stably support the vapor guiding head and facilitates the robotic arm to drive the catcher to move.

Further, the ejector pin assembly comprises an ejector pin cylinder and an adapter sealing member. The adapter sealing member is connected to a piston rod of the ejector pin cylinder, the vapor channel is disposed on the adapter sealing member, and when the catcher is located at the smoking position, the adapter sealing member is in sealing connection to a vapor outlet end of the catcher, and the vapor channel communicates the catcher with the smoking apparatus. This structure can quickly push the catcher to the smoking position and enable the catcher to be in sealing connection to the vapor channel.

Preferably, the smoking machine for an electronic cigarette further comprises an electronic cigarette triggering system, the electronic cigarette triggering system comprises a cigarette triggering portion and a triggering control cylinder connected to the cigarette triggering portion, the cigarette triggering portion is able to come into contact with the electronic cigarette under control of the triggering control cylinder, the triggering control cylinder is fixed on a connection block, and the connection block is connected to the housing by using a connection structure. A dedicated electronic cigarette triggering system is installed on the housing, so that automatic control of electronic cigarette triggering is implemented, and a problem that an existing smoking machine does not have a manually triggered electronic cigarette triggering system and external power supply is resolved.

Further, the cigarette triggering portion comprises a negative contact terminal and a positive contact terminal, the negative contact terminal corresponds to a position of a negative electrode of the electronic cigarette, the positive contact terminal corresponds to a position of a positive electrode of the electronic cigarette, and the negative contact terminal and the positive contact terminal are connected to a current control apparatus. In this technical solution, a steady direct current supplied by the current control apparatus of the smoking machine is used. Power is supplied to the cigarette cartridge connected to the electronic cigarette rod in a manner in which the positive contact terminal and the negative contact terminal are respectively in contact with the positive electrode and negative electrode of the electronic cigarette. This solution makes a measurement process continuous and stable, and measurement data is accurate and effective. In addition, in the foregoing technical solution, parameters such as a voltage, a current, and power can be adjusted and set by using the current control apparatus, the temperature of a heating wire can be changed, atomization efficiency of tobacco tar under different electric quantities can be examined, and a technical basis is provided for research and development of a product.

Further, the cigarette triggering portion comprises a cigarette pressing terminal, and the cigarette pressing terminal corresponds to a position of a power-on button of the electronic cigarette. The foregoing solution is used to trigger the electronic cigarette, and a pre-triggering time may be set pinpointing to a millisecond level, an advance amount of a specified triggering time may be implemented, thereby eliminating a delay problem of the triggering time and more accurately cooperating with a smoking starting time of the smoking machine.

Preferably, the clamping mechanism body comprises a horizontal base plate and a vertical supporting plate, an upper surface of the horizontal base plate is provided with a guiding groove, the guiding groove is disposed in a direction of the length of the horizontal base plate; and a bottom portion of the vertical supporting plate is connected to a rear end of the horizontal base plate, and the vertical supporting plate is provided with a base through hole penetrating in a horizontal direction; the other end of the cigarette clamp is a disc body connection end, and the disc body connection end penetrates into the base through hole of the vertical supporting plate; and the cigarette clamping mechanism further comprises a cigarette gripper, and the cigarette gripper comprises a gripper base plate and two side surface clamping portions disposed opposite to each other provided on the gripper base plate, the gripper base plate is installed on the guiding groove of the horizontal base plate and is movable in a direction of the length of the guiding groove, and the two side surface clamping portions are symmetrically disposed by using a vertical plane of a central axis of the axial through hole as a central axial plane.

The smoking end of a cigarette is inserted into the cigarette clamping end of the cigarette clamp. Since the two side surface clamping portions are symmetrically disposed by using a vertical plane of a central axis of the axial through hole as an axial plane, after the two side surface clamping portions disposed opposite to each other clamp side surfaces of the cigarette, a central axis of the cigarette can accurately align with the axial through hole on the cigarette clamp, keeping the cigarette airtight all the time after being inserted into the cigarette clamp and keeping a position of the cigarette to be stable. In addition, since the gripper base plate is movable along the direction of the length of the guiding groove, a position at which the two side surface clamping portions clamp the cigarette can change based on a structure of the cigarette. This enables cigarette clamping mechanism consistent with the present invention to clamp cigarettes of various types.

The rotary disc consistent with the present invention is perpendicular to the horizontal plane, and the electronic cigarette circumferentially rotates along with the rotary disc in a smoking experiment process, so that tobacco tar in a cigarette cartridge flows and fully immerses the oil guiding cotton, thus ensuring sufficient and steady supply of the tobacco tar to an atomizer, and guaranteeing atomization efficiency, atomization amount, and the stability and accuracy of experiment data. The cigarette clamping mechanism cooperates with a rotation direction of the rotary disc to stably clamp the electronic cigarette. The automatic loading and weighing system of the catcher cooperates with an operation direction of the rotary disc to control the catcher to move to a required position. In addition, a ventilation direction of the catcher is always consistent with a smoking experiment direction of the electronic cigarette. This can ensure that the catcher is quickly and stably changed during a smoking interval of two puffs, and can also ensure that the catcher returns to the smoking position after a weighing action is completed during the smoking interval of two puffs. The electronic cigarette triggering system consistent with the present invention implements automatic control of triggering of the electronic cigarette and resolves a problem that an existing smoking machine does not have a manually triggered electronic cigarette triggering system and external power supply.

DESCRIPTION OF REFERENCE NUMERALS

Figure 1:
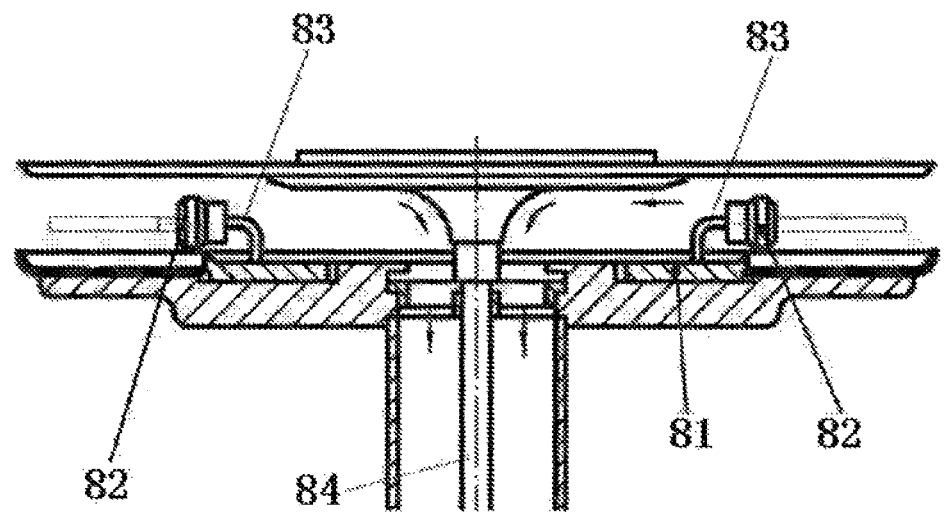
FIG. 1 is a schematic structural diagram of an existing rotary-disc smoking machine.
Figure 2:
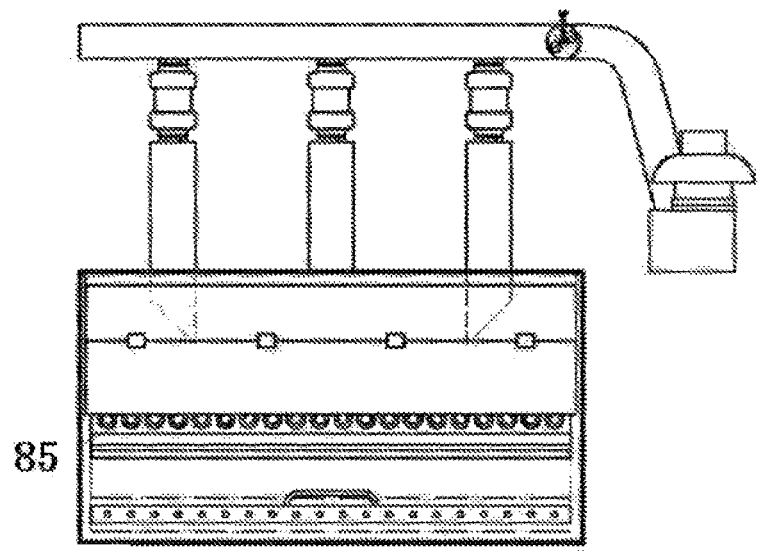
FIG. 2 is a schematic structural diagram of an existing linear smoking machine.

1 Electronic cigarette
11 Negative electrode
12 Positive electrode
13 Power-on button
2 Catcher
21 Catching body
22 Vapor guiding head
300 Main control circuit board
100 Housing
110 Sealing installment hole
200 Rotary disc
210 Disc-body smoking through hole
220 Housing connection hole
120 Housing sealing member
121 Sealing ventilation hole
122 Sealing core
123 Ring-shaped spring
124 Sealing portion O-shaped spring
125 Spiral cap
126 Catching sealing O-shaped spring
310 Clamping mechanism body
311 Horizontal base plate
312 Guiding groove
313 Guiding through hole
314 Vertical supporting plate
315 Base through hole
320 Cigarette clamp
321 Cigarette clamping end
322 Axial through hole
323 Labyrinth ring
324 Disc body connection end
330 Cigarette gripper
331 Gripper base plate
332 Fastening hole
333 Protruding portion
334 Side surface clamping portion
335 Spring plate
336 Guiding member
338 Fastening member
400 Ejector pin assembly
410 Ejector pin cylinder
420 Adapter sealing member
421 Vapor channel
430 Vapor guiding connection rod
440 Smoking apparatus
510 Temporary feeding storage store
511 Feeding guiding groove
512 Rotary stopper
513 Feeding identification apparatus
514 Stopping portion
520 Temporary discharge storage store 521 Discharge guiding groove
522 Ejecting and pushing stopper
523 Discharge identification apparatus
524 Limiting member
600 Transmission mechanism
610 Robotic arm
611 Gripper
620 Vertical guiding plate
621 Vertical guiding rail
630 Horizontal supporting plate
640 Vertical driving shaft
650 Vertical driving motor
660 Horizontal guiding rod
670 Horizontal driving motor
680 Horizontal guiding plate
681 Horizontal guiding rail
700 Balance
710 Adapter
711 Supporting plane
800 Discharge transferring mechanism
810 Inclined slideway
820 Discharge pushing cylinder
3 Cigarette triggering portion
31 Negative contact terminal
32 Positive contact terminal
33 Cigarette pressing terminal
4 Triggering control cylinder
41 Piston rod
5 Connection block
6 Connection structure
61 Fixed rod
62 Guiding rail
7 Integrated block
1001 Electronic cigarette rod
101 Positive electrode pipe
1011 Positive electrode pipe rear segment
1012 Positive electrode pipe front segment
102 Negative electrode pipe
103 Threaded head
1031 Limiting protruding ring
104 First insulation ring
105 Adapter
1051 Negative connection pipe
1052 Positive connection pipe
1053 Fourth insulation ring
106 Second insulation ring
201 Cigarette cartridge
2011 Atomization cavity
2012 Electronic cigarette pipe
2013 Electronic cigarette cap
2014 Thermal resistor
2015 Positive wiring
2016 Negative wiring
2017 Positive conductive pipe
2018 Negative conductive pipe
2019 Positioning protruding ring
2020 Third insulation ring
2221 Cigarette cartridge smoking channel
81 Rotary disc
82 Cigarette clamp
83 Smoke transmission bending pipe
84 Rotary axis
85 Smoking hole channel

DETAILED DESCRIPTION OF THE PREFERRED EMBODIMENTS

Implementations of the present invention are described below with reference to specific embodiments, and those skilled in the art can easily understand other advantages and effects of the present invention based on contents disclosed by the present specification.

Please refer to the accompanying drawings. It should be noted that the structures, proportions, sizes, and the like shown in the accompanying drawings of this specification are merely used for cooperating with the contents disclosed by this specification for understanding and reading by those skilled in the art and are not intended to set a limited condition for implementing the present invention. Therefore, the structures, proportions, sizes, and the like do not have substantial meanings technically. Any modification of the structures, change of a proportion relationship, or adjustment of the sizes without affecting the effects that can be generated and the objective that can be achieved by the present invention shall still fall within the scope that can be covered by the technical contents disclosed by the present invention. In addition, the terms such as "up", "down", "left", "right", "middle", and "one" cited in this specification are merely for convenience of description and are not intended to limit the implementable scope of the present invention, and a change or adjustment of a relative relationship thereof without a substantial technical content change shall also be considered as the implementable scope of the present invention.

As shown in FIG. 3 to FIG. 12, FIG. 19 and FIG. 30, a smoking machine for an electronic cigarette according to an embodiment comprises:

a housing 100;

a rotary disc 200 installed on a side surface of the housing, the rotary disc 200 rotates relative to the housing 100 with a central axis of the rotary disc as a center;

at least one disc-body smoking through hole 210 is disposed on an end face of the rotary disc 200;

a housing sealing member 120 is disposed on a side surface of the housing 100, and a sealing ventilation hole 121 penetrating into an inner portion of the housing 100 is provided in the housing sealing member 120, when the sealing ventilation hole 121 is in communication with one end of a catcher 2, the other end of the catcher 2 is in communication with a smoking apparatus 440; and the central axis of the rotary disc 200 is parallel to a horizontal plane; and at least one cigarette clamping mechanism, comprising a clamping mechanism body 310 and a cigarette clamp 320 disposed on the clamping mechanism body 310, wherein the cigarette clamp 320 is installed on the disc-body smoking through hole 210 of the rotary disc 200, one end of the cigarette clamp 320 is a cigarette clamping end 321 for inserting therein an electronic cigarette 1 in a horizontal direction, the cigarette clamp 320 is provided with an axial through hole 322 penetrating in a horizontal direction for smoke to pass through, and the rotary disc 200 is able to rotate to a position to make the axial through hole 322 in communication with the sealing ventilation hole 121 of the housing sealing member 120.

The central axis of the rotary disc 200 consistent with the present invention is parallel to the horizontal plane, that is, a central line around which the rotary disc 200 rotates is parallel to the horizontal plane. The rotary disc 200 is provided with at least one disc-body smoking through hole 210. The disc-body smoking through hole 210 passes through two end faces of the rotary disc 200. The disc-body smoking through hole 210 is provided with the cigarette clamping mechanism for clamping the electronic cigarette 1. The axial through hole 322 of the cigarette clamp 320 on the cigarette clamping mechanism is disposed in the horizontal direction. When the axial through hole 322 of the cigarette clamp 320 rotates to a position aligning with the sealing ventilation hole 121, the axial through hole 322 can come into communication with the sealing ventilation hole 121. When the rotary disc 200 rotates for a circle, since the electronic cigarette 1 is clamped and fixed on the cigarette clamping mechanism, and the electronic cigarette 1 rolls for a circle relative to the housing 100 with the central axis of the rotary disc 200 as a center. Tobacco tar stored inside the electronic cigarette 1 flows along an inner wall of a tobacco tar storage cavity for a circle, automatically fully immersing a fiberglass tar guiding rope during flowing. This effectively resolves a smoke output stability problem generated by tobacco tar deposition of a conventional smoking machine, so that a test result is more accurate and close to a real smoking behavior.

At the same time, the catcher 2 is pushed to move in the horizontal direction to a smoking position, so that the catcher 2 is in communication with the sealing ventilation hole 121 of the housing sealing member 120. That is, during smoking, smoke goes into the catcher 2 in the horizontal direction from the axial through hole 322 of the cigarette clamp 320 and the sealing ventilation hole 121 of the housing sealing member 120. The catcher 2 and the electronic cigarette 1 can be coaxially arranged, which remarkably reduces bumping condensation deposition of aerosol in a bending pipe of a conventional smoking machine, reduces transmission losses, is beneficial to correctness of smoke detection analysis, and resolves a technical problem that is difficult to solve for a conventional smoking machine during smoking of the electronic cigarette 1.

To enable a structure of the entire smoking machine for an electronic cigarette to be more compact and appropriate, a central axis of the disc-body smoking through hole 210 is parallel to the central axis of the rotary disc 200; a central axis of a sealing installment hole 110 passes through a circular rotation track by which a center point of the disc-body smoking through hole 210 passes when the rotary disc 200 rotates; and the sealing ventilation hole 121 penetrates into the housing sealing member 120 in a horizontal direction.

To more stably control the rotary disc 200, the smoking machine for an electronic cigarette comprises a main control circuit board 300, the main control circuit board 300 is electrically connected to the rotary disc 200, and the main control circuit board 300 controls the rotary disc 200 to rotate.

In this embodiment, a center of the rotary disc 200 is further provided with a housing connection hole 220. The housing connection hole 220 is in nested connection to a base connected to the housing 100. The cigarette clamping end 321 of the cigarette clamp 320 is in axial concentric sealing connection to the corresponding disc-body smoking through hole 210 on the rotary disc 200 by using a clamping portion O-shaped spring.

The housing sealing member 120 comprises a sealing core 122. The sealing ventilation hole 121 passes through two end faces of the sealing core 122 in a horizontal direction. One end of the sealing core 122 close to the rotary disc 200 is provided with an annular concave groove, and the annular concave groove is located between an outer surface of the sealing core 122 and the sealing ventilation hole 121. The annular concave groove is sequentially provided with a ring-shaped spring 123, a sealing portion O-shaped spring 124, an annular wear-resistant member, and a spiral cap 125. When the rotary disc 200 rotates, the end face of the rotary disc 200 remains in great contact with a contact surface of the spiral cap 125, and the end face of the rotary disc 200 can perform sliding friction and is airtight. The ring-shaped spring 123 remains elastic and enables the end of the sealing core 122 close to the rotary disc 200 to have a certain scalability performance.

One end of the sealing core 122 far away from the rotary disc 200 axially forms a conical hole. A central portion of a conical torus of the conical hole forms a sealing ring-shaped concave groove. The sealing ring-shaped concave groove is provided with an adaptable catching sealing O-shaped spring 126, used to support a vapor inlet of the catcher 2 and keep airtight.

When two or more disc-body smoking through holes 210 exist, the two or more disc-body smoking through holes 210 are evenly arranged on the rotary disc 200, and distances between central axes of the disc-body smoking through holes 210 and the central axis of the rotary disc 200 are the same. When the rotary disc 200 rotates, this structure enables the axial through hole 322 of the cigarette clamp 320 to sequentially come into communication with the sealing ventilation hole 121 of the housing sealing member 120.

The housing sealing member 120 is disposed on an upper portion of a side surface of the housing 100, and a central axis of the sealing ventilation hole 121 and the central axis of the rotary disc 200 both pass through a vertical plane perpendicular to the horizontal plane. The catcher 2 is generally disposed inside from a top portion of the housing 100. To facilitate the catcher 2 to quickly move to the smoking position corresponding to the sealing ventilation hole 121 of the housing sealing member 120, the housing sealing member 120 is disposed on an upper portion of the housing 100, and the central axis of the sealing ventilation hole 121 and the central axis of the rotary disc 200 pass through the vertical plane. This structure enables the axial through hole 322 to move to a position close to the top portion of the housing 100 and come into communication with the sealing ventilation hole 121 of the housing sealing member 120. An end face of the housing sealing member 120 is in close contact with the end face of the rotary disc 200. During rotation of the rotary disc 200, it is ensured that a channel in which smoke flows is isolated from the outside atmosphere and no smoke leakage phenomenon happens.

In this embodiment, the rotary disc 200 is flat cylindrical, so that the two end faces of the rotary disc 200 are parallel and are planes. This facilitates the end face of the rotary disc 200 to be sealed with the sealing ventilation hole 121 of the housing sealing member 120 during rotation of the rotary disc 200.

The smoking machine for an electronic cigarette further comprises an automatic loading and weighing system of a catcher, and the automatic loading and weighing system of a catcher comprises: a temporary feeding storage store 510 and a temporary discharge storage store 520, which are disposed on the housing 100 of the smoking machine for an electronic cigarette and in communication with an inner portion of the housing 100; a transmission mechanism 600, a balance 700, an ejector pin assembly 400, and a discharge transferring mechanism 800, which are disposed inside the housing 100; and a main control circuit board 300 electrically connected to the ejector pin assembly 400, the transmission mechanism 600, the balance 700, the temporary feeding storage store 510, the temporary discharge storage store 520, and the discharge transferring mechanism 800, the temporary feeding storage store 510 receives the catcher 2 disposed from an outer portion of the smoking machine for an electronic cigarette, and the catcher 2 is taken out from the temporary discharge storage store 520; a robotic arm 610 is installed on the transmission mechanism 600, the robotic arm 610 obtains the catcher 2, and the transmission mechanism 600 drives the robotic arm 610 to move, so that the catcher 2 reaches a preparation position and a weighing position, and during moving of the catcher 2, a central axis of the catcher 2 remains in parallel to the central axis of the sealing ventilation hole 121; the balance 700 weighs the catcher 2 reaching the weighing position; the ejector pin assembly 400 pushes the catcher 2 to horizontally move to the smoking position, and the ejector pin assembly 400 is provided with a vapor channel 421 for sucking vapor; and the discharge transferring mechanism 800 transfers the catcher 2 to a discharge position of the temporary discharge storage store 520 in a vertical direction.

To enable the structure of the smoking machine to be compact, the temporary feeding storage store 510 and the temporary discharge storage store 520 may be disposed on a top surface of the housing 100, and the discharge transferring mechanism 800 transfers the catcher 2 to the discharge position of the temporary discharge storage store 520 in a vertical direction.

When the automatic loading and weighing system of a catcher consistent with the present invention is used, the catcher 2 is disposed in the temporary feeding storage store 510 from the outer portion of the smoking machine for an electronic cigarette. When the electronic cigarette 1 needs to be smoked, the main control circuit board 300 controls the transmission mechanism 600 to drive the robotic arm 610 to move from the preparation position to a supporting position close to the bottom of the temporary feeding storage store 510. The preparation position is an initial zero position. The position is a reference position from which the robotic arm 610 moves to other working positions and is used for calculating a moving distance. The main control circuit board 300 controls the catcher 2 in the temporary feeding storage store 510 to fall on the robotic arm 610. The robotic arm 610 carries the catcher 2 and returns to the preparation position. Subsequently, the main control circuit board 300 controls the ejector pin assembly 400 to push the catcher 2 to the smoking position, and the robotic arm 610 moves together, so that the catcher 2 comes into connection to a smoking end of the electronic cigarette 1 by using the housing sealing member 120, the vapor channel 421 comes into communication with the catcher 2, the smoking apparatus 440 sucks vapor from the electronic cigarette 1 by using the vapor channel 421, and vapor smoke of the electronic cigarette 1 is absorbed by the catcher 2. Based on a specified condition, after a quantity of puffs or cigarettes is smoked, the main control circuit board 300 controls the ejector pin assembly 400 to contract. The main control circuit board 300 controls the transmission mechanism 600 to drive the catcher 2 on the robotic arm 610 to spring to the preparation position, and then the catcher 2 moves downward to the weighing position of the balance 700. The robotic arm continues to move downward and is slightly separated from the catcher 2, and the balance weighs the catcher 2. After weighing is completed, the main control circuit board 300 controls the transmission mechanism 600 to drive the robotic arm 610 to rise and return to the preparation position. When smoking needs to be continued based on the specified condition, the main control circuit board 300 controls the ejector pin assembly 400 to eject the catcher 2 to the smoking position again to perform smoking. The smoking and weighing process is repeated based on a specified smoking condition. When the catcher 2 needs to be taken out when a smoking termination condition is reached, the catcher 2 is transmitted by the discharge transferring mechanism 800 to the discharge position of the temporary discharge storage store 520 by a discharge transferring mechanism.

Since a direction at which the central axis of the sealing ventilation hole 121 is located is a smoking experiment direction of the electronic cigarette 1, in the present invention, the catcher 2 falls on the robotic arm 610 located at a supporting position in a vertical direction, and in a process when the robotic arm 610 drives the catcher 2 to move to the preparation position, the weighing position, and the discharge position, the central axis of the catcher 2 remains in parallel to the central axis of the sealing ventilation hole 121. In this way, when the system consistent with the present invention is used, a ventilation direction of the catcher 2 is always consistent with the smoking experiment direction of the electronic cigarette 1. Therefore, the catcher 2 drops material and cooperates with the robotic arm 610 depending on the gravity, thereby ensuring that the catcher 2 is quickly and stably changed within a smoking interval of two puffs. That is, the electronic cigarette 1 changes the catcher 2 within 27 s of the smoking interval of two puffs.

The catcher 2 is always in an effective control range of the robotic arm 610 inside the smoking machine. Both of the transmission mechanism 600 and the balance 700 are located inside the housing 100. The weighing position and the smoking position are quite close. After smoking is completed, the robotic arm 610 can conveniently move the catcher 2 to the weighing position. After weighing is completed, the robotic arm 610 can move the catcher 2 to the smoking position again. An entire process in which the catcher 2 is moved to the weighing position to be weighed and then returns to the smoking position is controlled by the main control circuit board 300. Therefore, it may also be ensured that all actions are completed within a smoking interval of two puffs. That is, after transferring the catcher 2 from the smoking position to the weighing position to perform weighing within 27 s of the smoking interval of two puffs, then returning the catcher 2 to the smoking position.

The present invention provides an optimized cooperation relationship between rotation of the rotary disc 200 and the automatic loading and weighing system of the catcher 2. While conforming to a related standard rule of a single smoking duration and a smoking volume of the electronic cigarette 1, at least two test procedures may be implemented as follows. Procedure 1: When multiple electronic cigarettes 1 with a same brand and specification are loaded on the rotary disc 200, each of the multiple electronic cigarettes 1 may be continuously and sequentially smoked for one or more puffs. Released aerosol is caught by a filter of the catcher 2. In this process, a smoking interval of two puffs of a single electronic cigarette 1 needs to be longer than 27 s according to a rule. After the first puff of smoking of the first electronic cigarette 1 is completed, in a smoking interval when the second puff has not started, another electronic cigarette 1 may be smoked. When a set quantity of puffs of smoking of all electronic cigarettes 1 is completed, a catcher 2 is changed, and a next group of a set quantity of puffs of smoking is continued. It continues until all the electronic cigarettes 1 complete a total set quantity of puffs of smoking or service lives of all the electronic cigarettes 1 terminate, an analysis process of a single or several puffs of a mass of electronic cigarettes 1 is implemented, at the same time, detection time is greatly reduced. Procedure 2: Multiple electronic cigarettes 1 with different brands and specifications are loaded to each smoking hole channel on the rotary disc 200. A smoking process in which the electronic cigarettes 1 are sequentially smoked is set, that is, a next electronic cigarette is smoked after a single electronic cigarette 1 is completely smoked. During smoking process of a single electronic cigarette 1, the catcher 2 is automatically changed based on a quantity of puffs of smoking or a set value of a minimum catching amount. In such a manner, a continuous test process may complete each puff analysis, entire smoke analysis, and service life detection of multiple electronic cigarettes 1 with different brands and specifications.

The discharge transferring mechanism 800 comprises an inclined slideway 810 for the catcher 2 to slide and a discharge pushing cylinder 820, a horizontal height of an end of the inclined slideway 810 close to the temporary discharge storage store 520 is less than a horizontal height of an end of the inclined slideway 810 far away from the temporary discharge storage store 520, the discharge pushing cylinder 820 is disposed below the end of the inclined slideway 810 close to the temporary discharge storage store 520, a piston rod of the discharge pushing cylinder 820 is located exactly below the temporary discharge storage store 520, and the piston rod of the discharge pushing cylinder 820 is provided with a supporting portion supporting the catcher 2.

The inclined slideway 810 is disposed to quickly transfer the catcher 2 to the discharge position. After the robotic arm 610 places the catcher 2 at the end of the slideway 810 far away from the temporary discharge storage store 520, the catcher 2 slides along an inclined direction of the inclined slideway 810 to the end of the inclined slideway 810 close to the temporary discharge storage store 520. In this case, the piston rod of the discharge pushing cylinder 820 is exactly below the catcher 2. The main control circuit board 300 controls the piston rod of the discharge pushing cylinder 820 to push the catcher 2 in the vertical direction, so that the catcher 2 can be quickly pushed to the discharge position of the temporary discharge storage store 520.

As shown in FIG. 3, FIG. 15, FIG. 16, and FIG. 19, the temporary feeding storage store 510 is provided with a feeding guiding groove 511 to insert the catcher 2. A rotary stopper 512 that can rotate to release the catcher 2 and a feeding identification apparatus 513 that identifies a position of the catcher 2 are disposed in the feeding guiding groove 511. Both the rotary stopper 512 and the feeding identification apparatus 513 are electrically connected to the main control circuit board 300.

The rotary stopper 512 comprises a stopping portion 514 that can support the catcher 2 and prevent the catcher 2 from moving downward. When the rotary stopper 512 is controlled to rotate by 180 degrees, the stopping portion 514 also rotates for 180 degrees, so that the catcher 2 is not restricted by the stopping portion 514 and falls into an inner portion of the housing 100.

When the catcher 2 cannot move downward because the catcher 2 is stopped by the stopping portion 514 of the rotary stopper 512 in the feeding guiding groove 511, the feeding identification apparatus 513 transmits information of the catcher 2 in the feeding guiding groove 511 to the main control circuit board 300. The main control circuit board 300 controls the rotary stopper 512 to rotate by 180 degrees to release the catcher 2, so that the catcher 2 falls on the robotic arm 610 located at the supporting position inside the housing 100. The feeding guiding groove 511 limits the position of the catcher 2. Therefore, in the process that the catcher 2 enters the preparation position from the feeding guiding groove 511, the central axis of the catcher 2 is always parallel to a horizontal plane.

Figure 3:
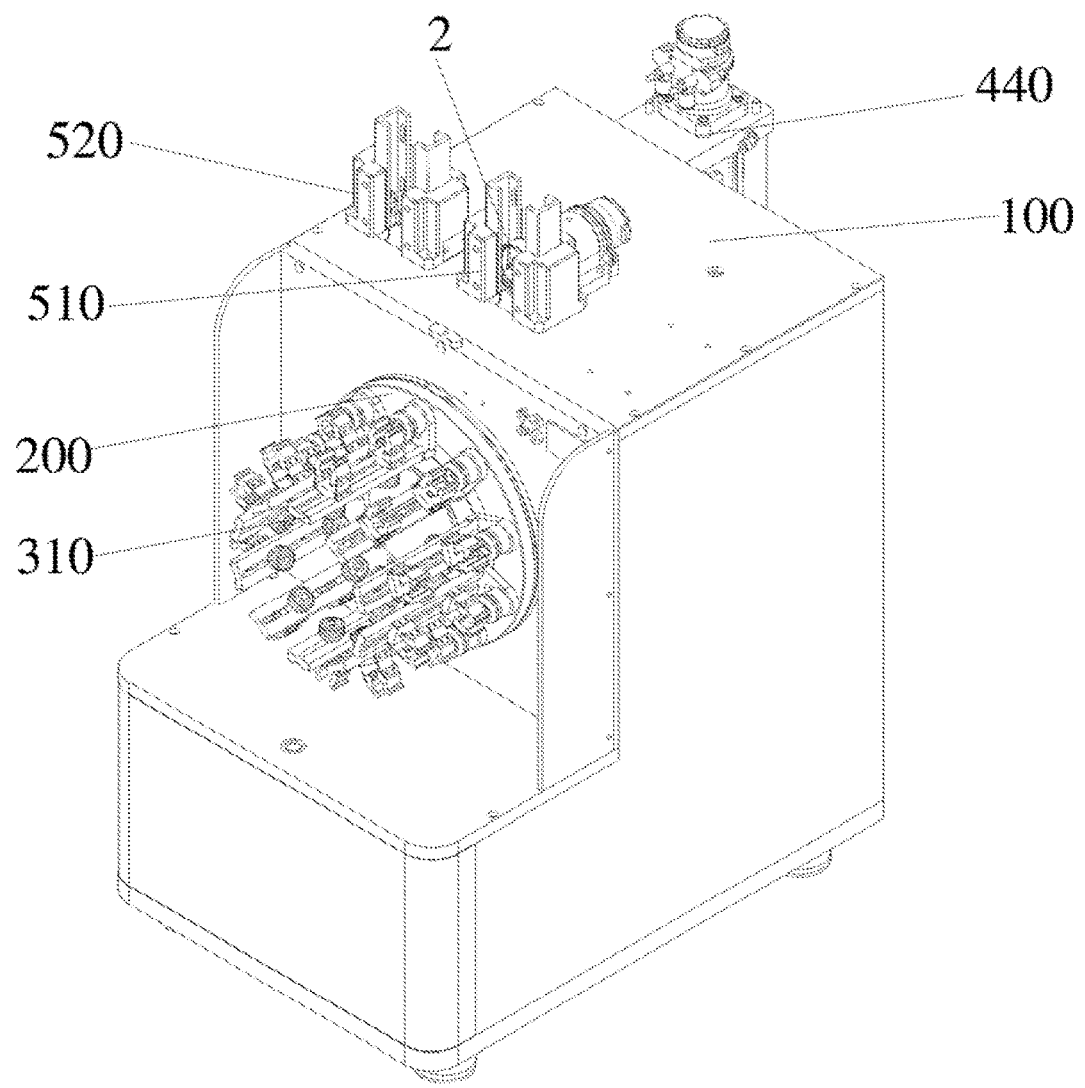
FIG. 3 is a schematic diagram of an external structure of a smoking machine for an electronic cigarette according to an embodiment.
Figure 4:
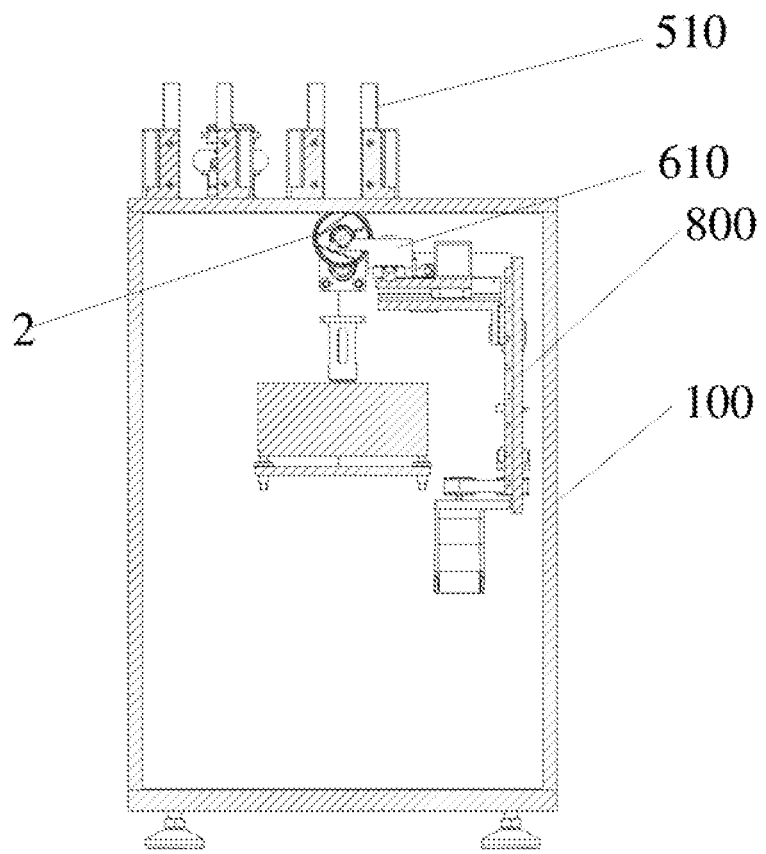
FIG. 4 is a schematic cross-sectional structural diagram when a catcher is located at a preparation position of an automatic changing and weighing system of a catcher in a smoking machine for an electronic cigarette according to an embodiment.
Figure 17:
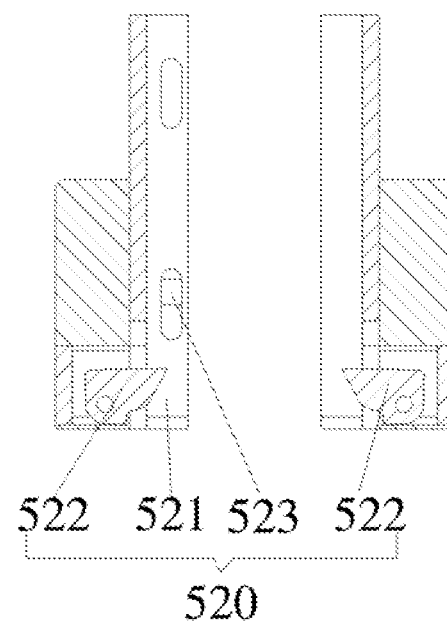
FIG. 17 is a schematic structural diagram when a limiting member of an automatic changing and weighing system of a catcher is located in an initial state in a smoking machine for an electronic cigarette according to an embodiment.
Figure 18:
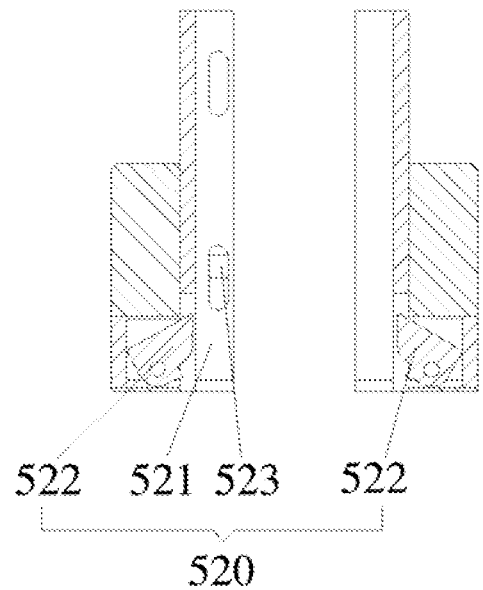
FIG. 18 is a schematic structural diagram when a limiting member of an automatic changing and weighing system of a catcher rotates to open after being pushed by a catcher in a smoking machine for an electronic cigarette according to an embodiment.
Figure 19:
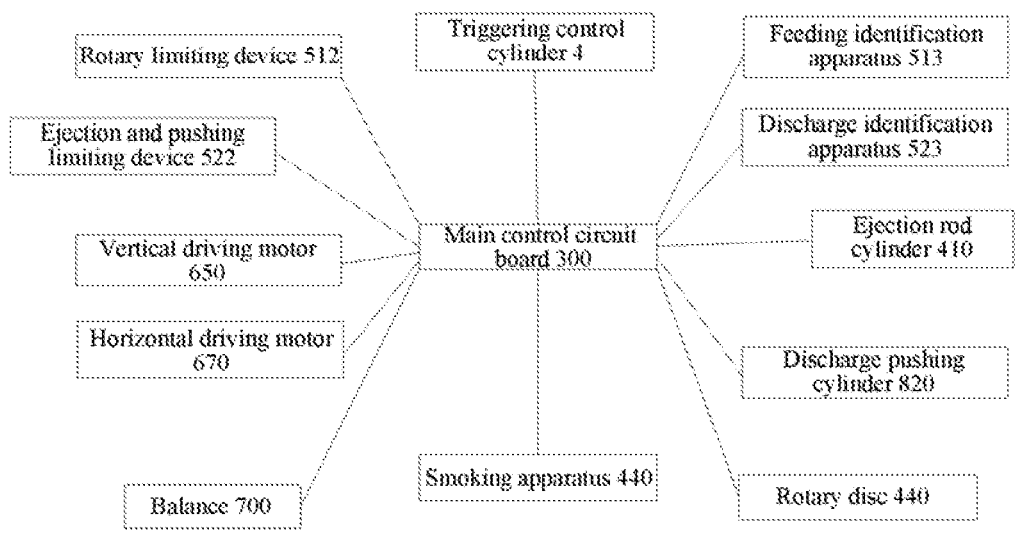
FIG. 19 is a flowchart of a smoking machine for an electronic cigarette operating under control of a main control circuit board according to an embodiment.
Figure 20:
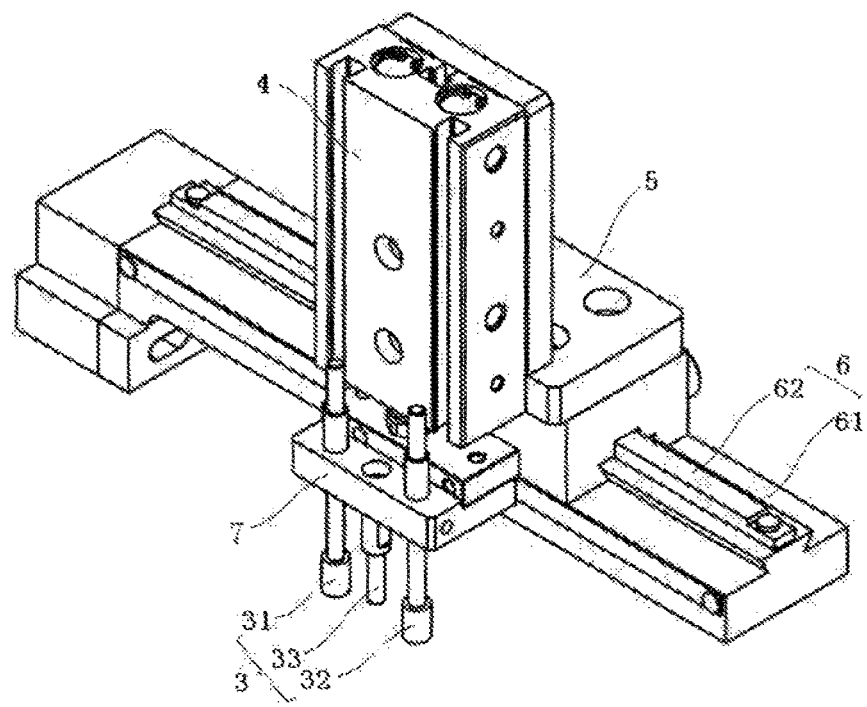
FIG. 20 is a schematic structural diagram of an electronic cigarette triggering system in a smoking machine for an electronic cigarette according to an embodiment.

As shown in FIG. 3, FIG. 17, and FIG. 19, the temporary discharge storage store 520 is provided with a discharge guiding groove 521 to insert the catcher 2. An ejecting and pushing stopper 522 that can be turned on when the catcher 2 pushes upward and a discharge identification apparatus 523 that identifies the position of the catcher 2 are disposed in the discharge guiding groove 521. Both the ejecting and pushing stopper 522 and the discharge identification apparatus 523 are electrically connected to the main control circuit board 300.

The ejecting and pushing stopper 522 comprises two limiting members 524 disposed opposite to each other in the discharge guiding groove 521. Both of the two limiting members 524 are movably connected to the discharge guiding groove 521. The length of an upper portion of the limiting member 524 in a horizontal direction is greater than the length of a lower portion of the limiting member 524 in a horizontal direction.

The catcher 2 is pushed by the piston rod of the discharge pushing cylinder 820 to the temporary discharge storage store 520. The catcher 2 may push the two limiting members 524 to rotate, so that the catcher 2 passes the two limiting members 524. After the catcher 2 is pushed to the discharge position, the main control circuit board 300 controls the two limiting members 524 to return to an original position and support the catcher 2. The piston rod of the discharge pushing cylinder 820 may quickly push the catcher 2 in a vertical direction to pass the two limiting members 524 to reach the discharge position of the discharge guiding groove 521.

Figure 5:
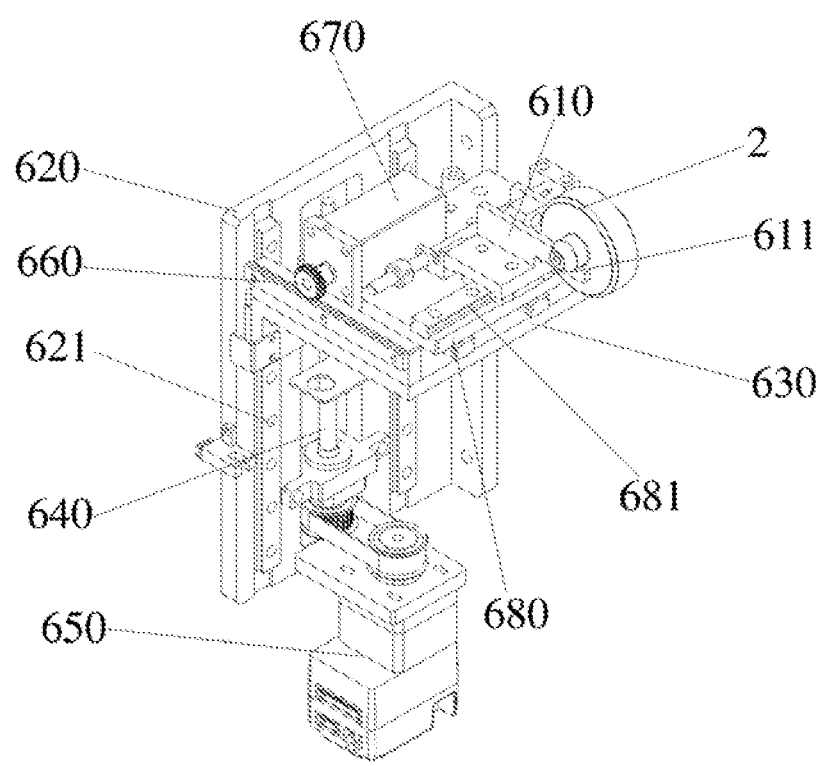
FIG. 5 is a schematic three-dimensional structural diagram when a catcher is located at a preparation position of an automatic changing and weighing system of a catcher in a smoking machine for an electronic cigarette according to an embodiment.
Figure 14:
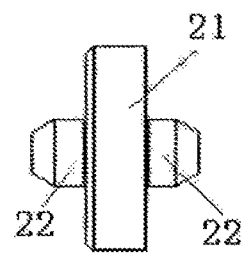
FIG. 14 is a schematic structural diagram of a catcher according to an embodiment.
Figure 15:
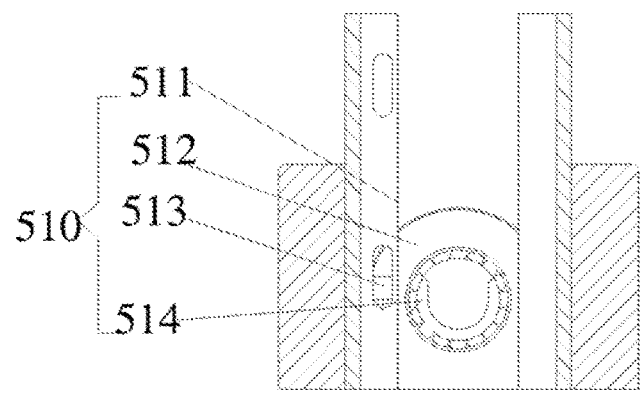
FIG. 15 is a schematic structural diagram when a rotary stopper in a temporary feeding storage store of an automatic changing and weighing system of a catcher does not rotate to release a catcher in a smoking machine for an electronic cigarette according to an embodiment.
Figure 16:
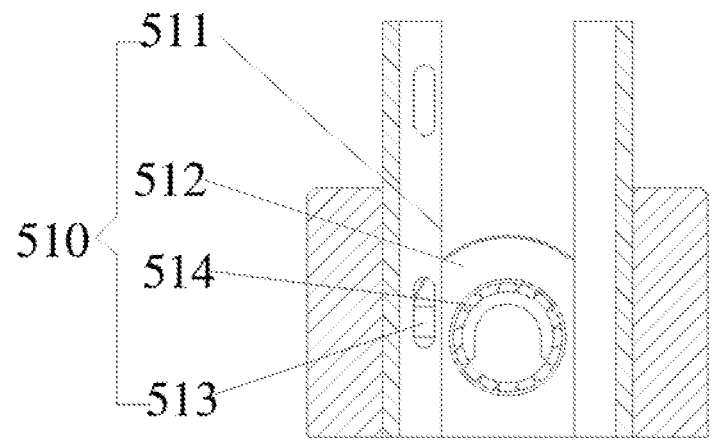
FIG. 16 is a schematic structural diagram after a rotary stopper in a temporary feeding storage store of an automatic changing and weighing system of a catcher rotates to release a catcher in a smoking machine for an electronic cigarette according to an embodiment.

As shown in FIG. 5 and FIG. 14, the catcher 2 comprises a catching body 21 and a vapor guiding head 22 disposed on each of two axial end faces of the catching body 21; the robotic arm 610 is formed by two gripers 611 with a V-shaped groove at an end portion; and the V-shaped groove supports the corresponding vapor guiding head 22. This structure enables the grippers 611 of the robotic arm 610 to stably support the vapor guiding head 22 and facilitate the robotic arm 610 to drive the catcher 2 to move.

Figure 8:
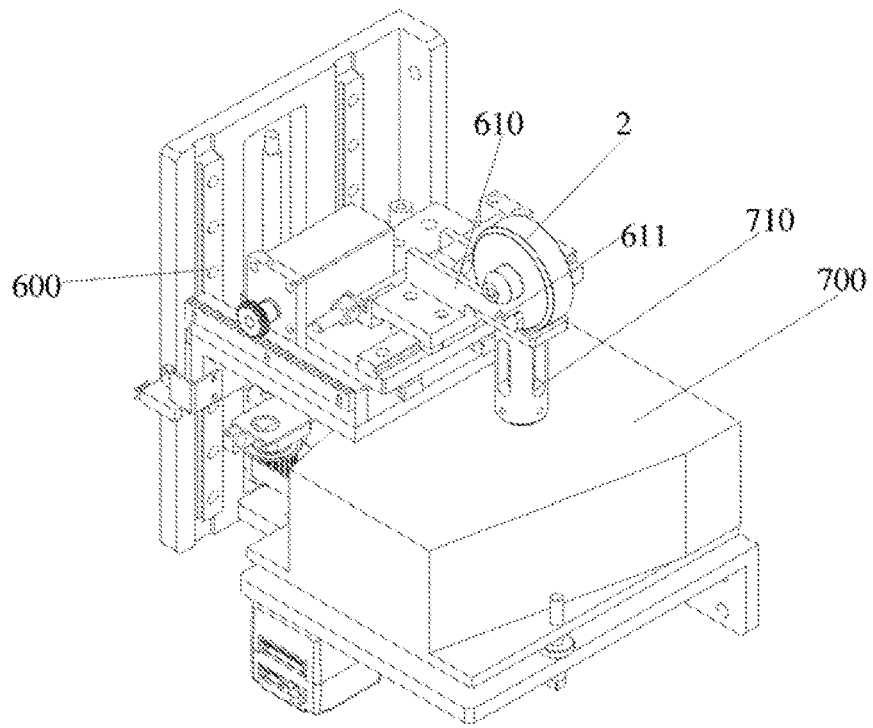
FIG. 8 is a schematic three-dimensional structural diagram when a catcher is located at a weighing position of an automatic changing and weighing system of a catcher in a smoking machine for an electronic cigarette according to an embodiment.
Figure 9:
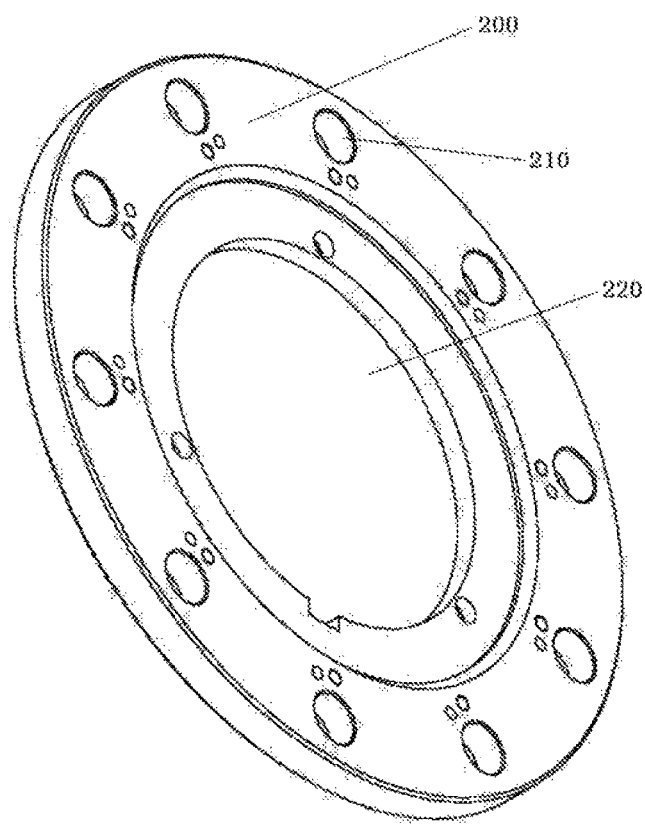
FIG. 9 is a schematic structural diagram of a rotary disc of a smoking machine for an electronic cigarette according to an embodiment.
Figure 10:
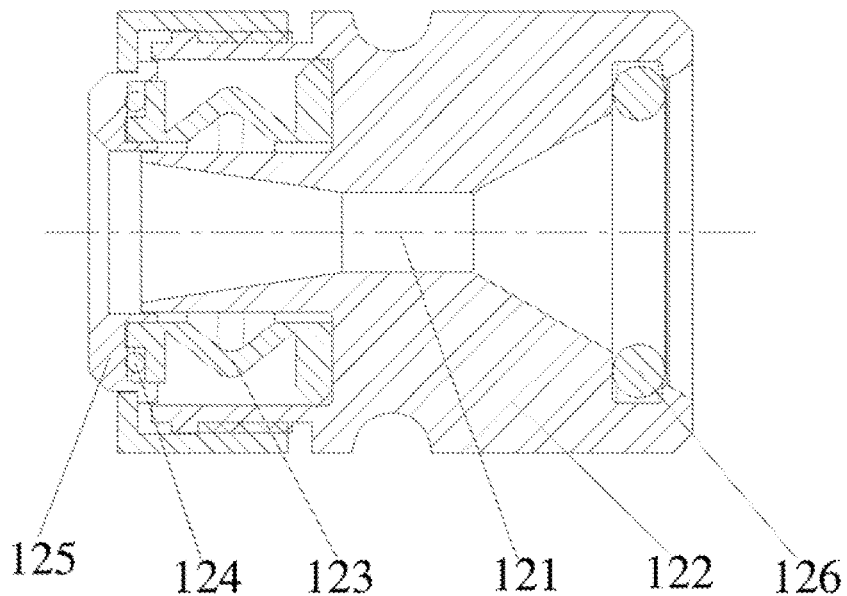
FIG. 10 is a schematic structural diagram of a housing sealing member of a smoking machine for an electronic cigarette according to an embodiment.
Figure 11:
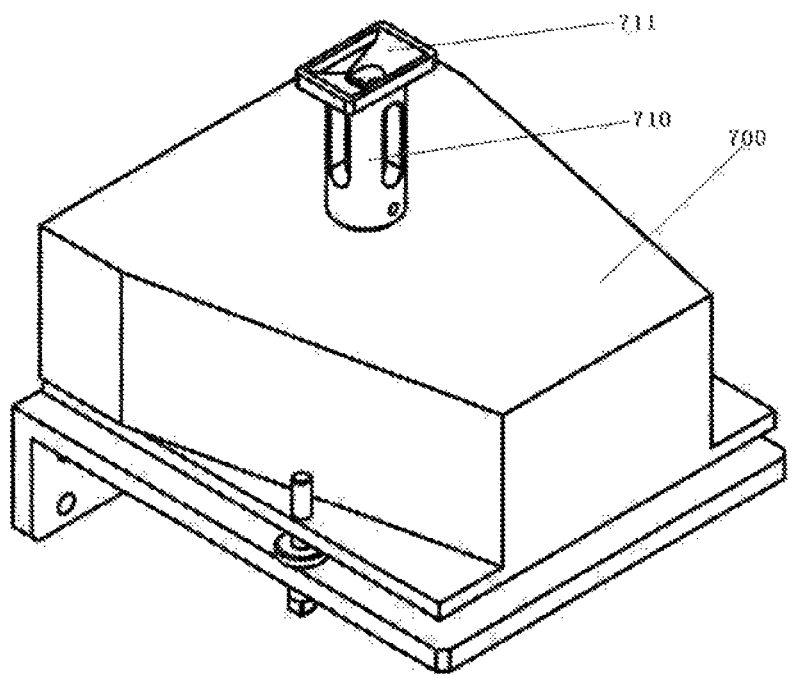
FIG. 11 is a schematic structural diagram of a balance of an automatic changing and weighing system of a catcher in a smoking machine for an electronic cigarette according to an embodiment.
Figure 12:
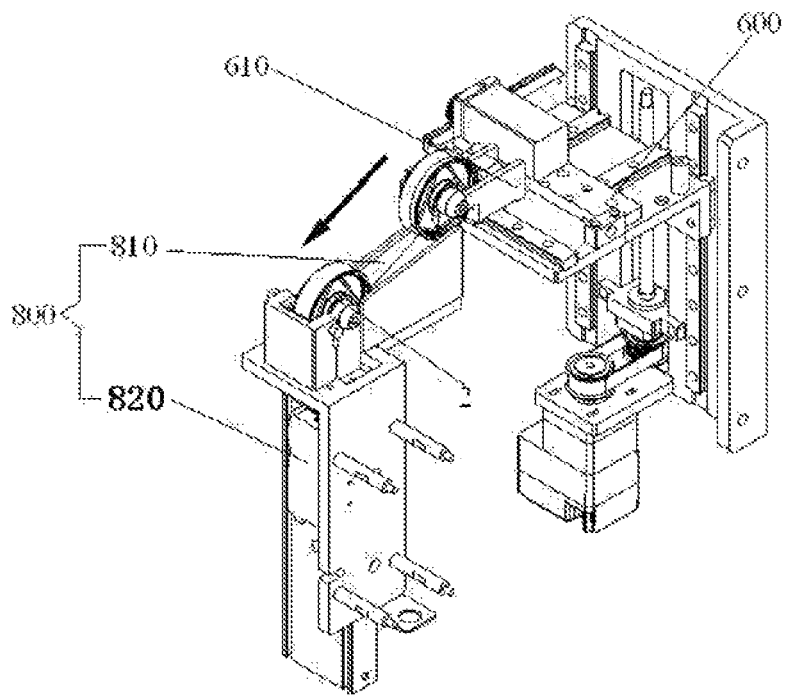
FIG. 12 is a schematic structural diagram of a catcher sliding on an inclined slideway of an automatic changing and weighing system of a catcher in a smoking machine for an electronic cigarette according to an embodiment.
Figure 13:
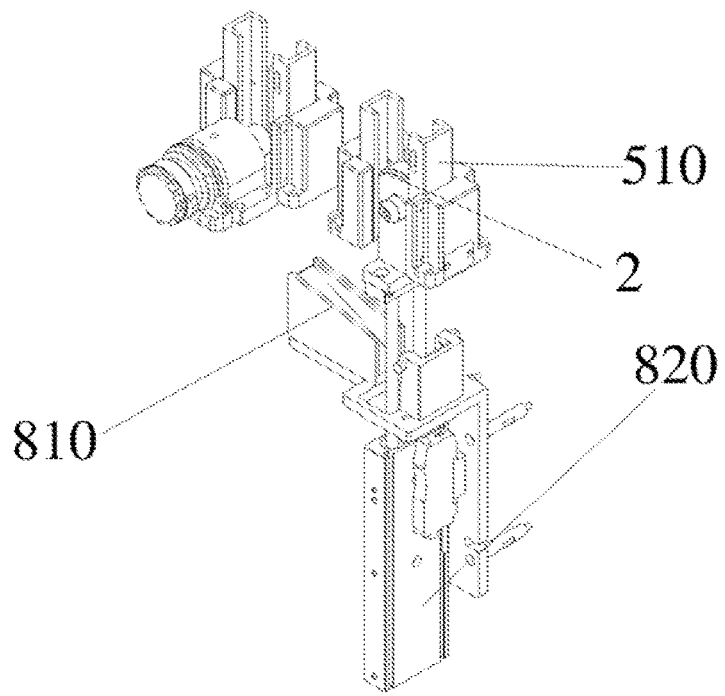
FIG. 13 is a schematic structural diagram when a catcher is located at a discharging position of an automatic changing and weighing system of a catcher in a smoking machine for an electronic cigarette according to an embodiment.

As shown in FIG. 8, FIG. 9, and FIG. 12, since a side surface of the catching body 21 is arc-shaped. A weighing end of the balance 700 is provided with an adapter 710 corresponding to the catcher 2. The shape of a supporting surface 711 of the adapter 710 corresponds to the shape of a side surface of the catching body 21. The supporting surface 711 is arc-shaped. This structure enables the side surface of the catching body 21 of the catcher 2 to be stably placed on the adapter 710, thereby facilitating weighing of the catcher 2.

To facilitate weighing of the catcher 2 after smoking is completed, the balance 700 is located below the preparation position, so that the robotic arm 610 quickly moves from the smoking position to the weighing position by passing the preparation position.

Figure 6:
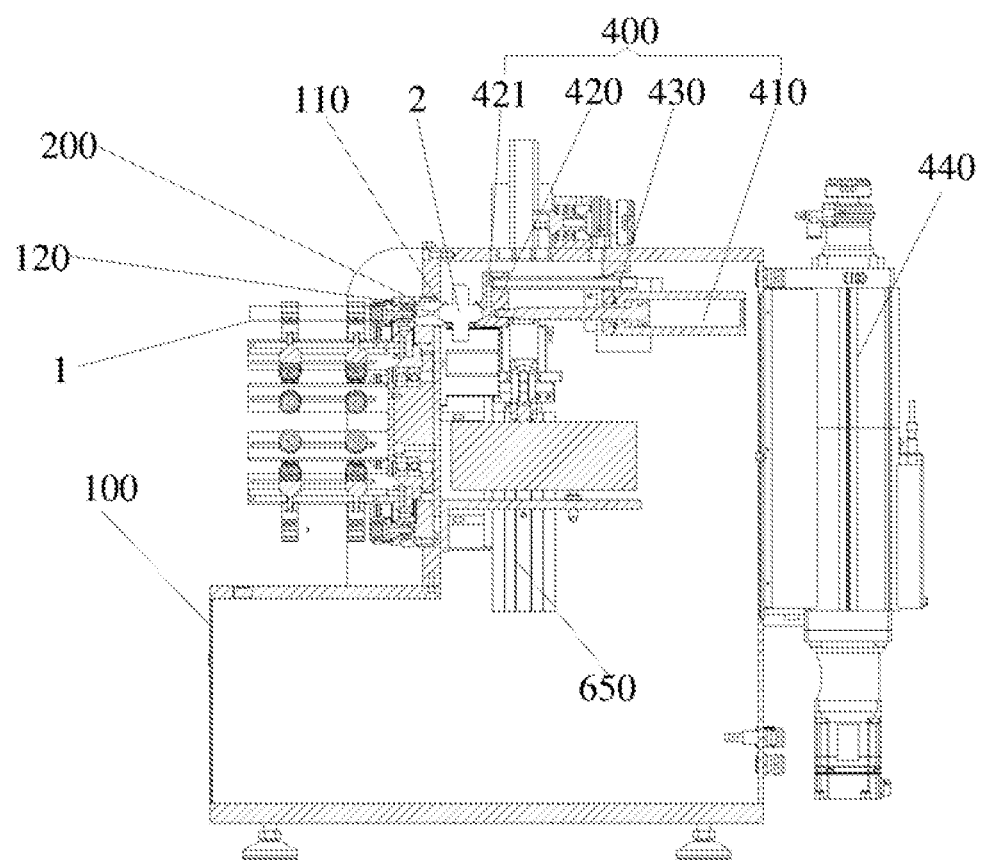
FIG. 6 is a schematic cross-sectional structural diagram of a smoking machine for an electronic cigarette according to an embodiment.
Figure 7:
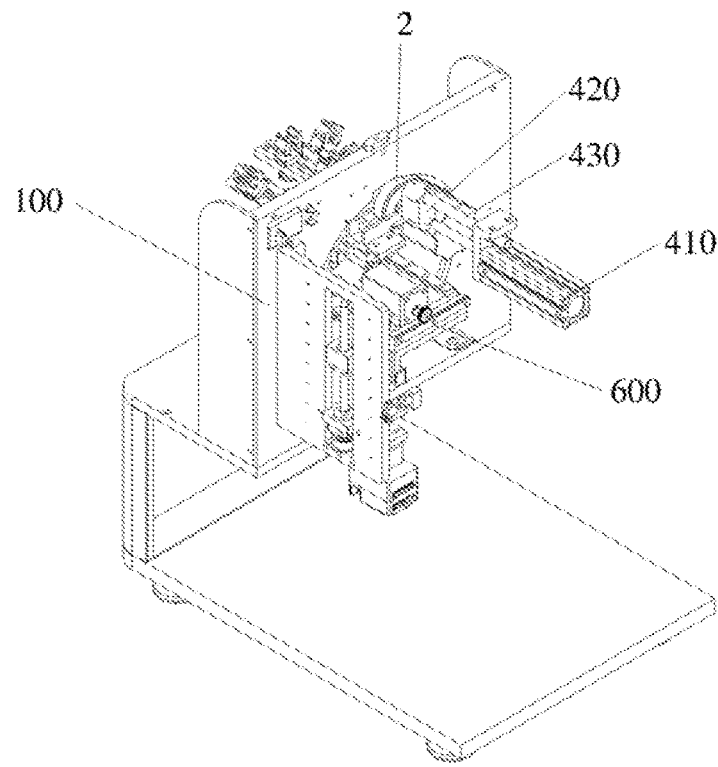
FIG. 7 is a schematic three-dimensional structural diagram when a catcher is located at a smoking position of an automatic changing and weighing system of a catcher in a smoking machine for an electronic cigarette according to an embodiment.

As shown in FIG. 6, FIG. 7, and FIG. 19, the ejector pin assembly 400 comprises an ejector pin cylinder 410 and an adapter sealing member 420. The adapter sealing member 420 is connected to a piston rod 41 of the ejector pin cylinder 410, and the vapor channel 421 is disposed on the adapter sealing member 420. When the catcher 2 is located at the smoking position, the adapter sealing member 420 is in sealing connection to a vapor outlet end of the catcher 2, and the vapor channel 421 communicates the catcher 2 with the smoking apparatus 440. This structure can quickly push the catcher 2 to the smoking position and enable the catcher 2 to be in sealing connection to the vapor channel 421.

The adapter sealing member 420 is connected to the smoking apparatus 440 by using a vapor guiding connection rod 430, and the vapor guiding connection rod 430 is in communication with the vapor channel 421. The smoking apparatus 440 is in communication with the vapor channel 421 on the adapter sealing member 420 by using the vapor guiding connection rod 430. After smoking is performed, vapor smoke of the electronic cigarette 1 is absorbed by the catcher 2. Both of the smoking apparatus 440 and the ejector pin cylinder 410 are electrically connected to the main control circuit board 300.

As shown in FIG. 5 and FIG. 19, the transmission mechanism 600 comprises: a vertical guiding plate 620, the vertical guiding plate 620 is provided with a vertical guiding rail 621; a horizontal supporting plate 630, which is installed on the vertical guiding rail 621, and the horizontal supporting plate 630 can vertically move along the vertical guiding rail 621, the horizontal supporting plate 630 is connected to a vertical driving shaft 640, and the vertical driving shaft 640 is connected to a vertical driving motor 650; a horizontal guiding rod 660, which is disposed on the horizontal supporting plate 630; a horizontal guiding plate 680, which is movably connected to the horizontal supporting plate 630, and the horizontal guiding plate 680 can horizontally move on the horizontal supporting plate 630; a horizontal driving motor 670, which is connected to the horizontal guiding plate 680, an output axis of the horizontal driving motor 670 is movable along the horizontal guiding rod 660 in a horizontal direction; and a horizontal guiding rail 681, which is disposed on the horizontal guiding plate 680, a direction at which a central axis of the horizontal guiding rail 681 is located is perpendicular to a direction in which the horizontal guiding plate 680 horizontally moves on the horizontal supporting plate 630. The robotic arm 610 is movably connected to the horizontal guiding rail 681 by using a spring, and the robotic arm 610 is movable along the horizontal guiding rail 681. Both of the vertical driving motor 650 and the horizontal driving motor 670 are electrically connected to the main control circuit board 300.

The vertical driving motor 650 drives the horizontal supporting plate 630 to move in a vertical direction by using the vertical driving shaft 640. The horizontal driving motor 670 drives the horizontal guiding plate 680 to move along the horizontal guiding rod 660. The robotic arm 610 can drive the catcher 2 to move along the horizontal guiding rail 681. Since the direction at which the central axis of the horizontal guiding rail 681 is located is perpendicular to the direction in which the horizontal guiding plate 680 horizontally moves on the horizontal supporting plate 630, therefore, the transmission mechanism 600 can enable the robotic arm 610 to drive the catcher 2 to quickly move in three directions perpendicular to each other. In this way, the catcher 2 can quickly move to a required position.

A usage method of the automatic changing and weighing system of a catcher according to the present embodiment comprises the following steps.

As shown in FIG. 3 to FIG. 5, FIG. 15, FIG. 16, and FIG. 19, the catcher 2 is disposed at a feeding position in the temporary feeding storage store 510 from an outer portion of the smoking machine for an electronic cigarette. After the feeding identification apparatus 513 transmits detected information indicating that the catcher 2 is located at the feeding position to the main control circuit board 300, the main control circuit board 300 controls the transmission mechanism 600 to drive the robotic arm 610 to move to the supporting position close to the bottom portion of the temporary feeding storage store 510. The main control circuit board 300 controls the rotary stopper 512 of the temporary feeding storage store 510 to rotate by 180 degrees. After the stopping portion 514 rotates for 180 degrees, the catcher 2 falls on the robotic arm 610, so that the catcher 2 reaches the supporting position. Subsequently, the main control circuit board 300 controls the robotic arm 610 to carry the catcher 2 and move to the preparation position.

As shown in FIG. 6, FIG. 7, and FIG. 19, when the electronic cigarette 1 needs to be smoked, the main control circuit board 300 controls the ejector pin assembly 400 to push the catcher 2 to the smoking position in a horizontal direction. The robotic arm 610 moves with the catcher 2, and a spring (not shown in the figures) of the robotic arm 610 connected to the horizontal guiding rail 681 contracts. The catcher 2 is connected to the smoking end of the electronic cigarette 1. The vapor channel 421 of the ejector pin assembly 400 is in communication with the catcher 2. The main control circuit board 300 controls the smoking apparatus 440 to smoke the electronic cigarette 1 by using the vapor channel 421, so that vapor smoke of the electronic cigarette 1 enters the catcher 2 and is absorbed by the catcher 2.

As shown in FIG. 4, FIG. 5, FIG. 8, FIG. 11, and FIG. 19, when smoking is completed, the main control circuit board 300 controls the ejector pin assembly 400 to contract. The spring of the robotic arm 610 connected to the horizontal guiding rail 681 extends, and the robotic arm 610 drives the catcher 2 to return to the preparation position. The main control circuit board 300 controls the transmission mechanism 600, so that the transmission mechanism 600 drives the catcher 2 on the robotic arm 610 to move to the weighing position of the balance 700. The main control circuit board 300 controls the robotic arm 610 to release the catcher 2, and the balance 700 measures the weight of the catcher 2.

As shown in FIG. 12, FIG. 13, and FIG. 17 to FIG. 19, when the catcher 2 needs to be taken out, the main control circuit board 300 controls the robotic arm 610 by using the transmission mechanism 600, so that the catcher 2 moves to an end of the inclined slideway 810 far away from the temporary discharge storage store 520. The robotic arm 610 releases the catcher 2, and the catcher 2 slides along the inclined slideway 810 to the supporting portion of the discharge pushing cylinder 820. The main control circuit board 300 controls the piston rod of the discharge pushing cylinder 820 to move upward to drive the catcher 2 to push the ejecting and pushing stopper 522 in the temporary discharge storage store 520 to open. That is, the two limiting members 524 rotate, so that the catcher 2 moves upward to the discharge position of the temporary discharge storage store 520. The discharge identification apparatus 523 transmits detected information indicating that the catcher 2 is located at the discharge position to the main control circuit board 300. The main control circuit board 300 controls the two limiting members 524 to return to an initial position and support the catcher 2 below the catcher 2.

As shown in FIG. 2 to FIG. 19, a quantity of smoking puffs of the electronic cigarette 1 is far greater than that of a conventional cigarette, and generally comprises at least 150 or more than 150 puffs. A fiberglass Cambridge filter having a diameter of 44 mm well known in this professional technical field is generally used for catching smoke, and a theoretical smoke carrying amount of the fiberglass Cambridge filter is 150 mg. To avoid a diafiltration phenomenon caused when a smoke catching amount exceeds a filter bearing amount in a continuous measurement process, a catcher 2 provided with a Cambridge filter needs to be changed after a quantity of smoking puffs. Therefore, the temporary feeding storage store 510 and the temporary discharge storage store 520 of the catcher 2 designed by the present invention are vertically arranged on the top portion of the housing 100. An axial direction of the catcher 2 is consistent with a direction of the catcher 2 in a smoking experiment. A direction of the vapor inlet of the catcher 2 keeps facing the rotary disc 200. The catcher drops material and cooperates with the robotic arm 610 depending on the gravity, thereby ensuring that the catcher 2 is quickly and stably changed within a smoking interval of two puffs.

In the continuous measurement process, when a quality change of the catcher 2 in the smoking process needs to be monitored before the catcher 2 is changed, that is, when an amount change occurs on smoke of the electronic cigarette 1, the catcher 2 needs to be weighed at an interval of a quantity of smoking puffs (for example, 1, 2, 3, . . . puffs). In this case, the catcher 2 must be removed from a smoking working position originally sealed between the smoking hole channel and a smoking unit of the electronic cigarette 1 and be loaded at the original smoking working position and sealed again after being weighed. According to a rule in a well known related detection standard or method in this professional technical field, generally, a maximum interval of two smoking puffs does not exceed 1 min., and an interval between two smoking puffs of the electronic cigarette 1 is generally stipulated as 27s. When a conventional smoking machine is used to smoke the electronic cigarette 1, if the catcher 2 needs to be weighed, the catcher 2 needs to be taken manually or by using the robotic arm 610 and is manually weighed. Neither can ensure that the catcher 2 can be returned to the smoking working position for smoking again after the catcher 2 is weighed within the time limit. Therefore, an advantage consistent with the present invention lies in that the catcher 2 is always in and quite close to an effective control range of the robotic arm 610 inside the smoking machine. The balance 700 disposed inside the smoking machine and the adapter 710 of the balance 700 used to support the catcher 2 are disposed below and quite close to the smoking working position. During smoking, the catcher 2 is pushed to the smoking working position by the ejector pin assembly 400 located at a direction of a vapor outlet of the catcher 2. During weighing, the ejector pin cylinder 410 releases an ejector pin. The catcher 2 is supported by the robotic arm 610 and is quickly sent to the adapter 710 supported by the balance 700. After the weighing is completed, the catcher 2 is returned by the robotic arm 610, and the ejector pin assembly 400 is tightly pushed again. During this process, a data collection process of transferring and weighing of the catcher 2 is fully and automatically completed by an instrument, thereby ensuring that all actions are completed within the smoking interval of two puffs.

By using the system consistent with the present invention, a method for determining smoking determination by using a weighting method may be implemented, so as to resolve a determining problem of smoking determination of the electronic cigarette 1: A conventional cigarette generates smoke by burning a tobacco segment of the cigarette. Therefore, when the cigarette is burned to a cigarette stub length defined by a standard, a cotton thread in close contact with an outer surface of the cigarette and located at a termination position is burned away to trigger a micro switch, or an infrared sensor disposed at a corresponding position is triggered to terminate smoking. The largest value in the following three sets of data is used as the cigarette stub length determining smoking termination: 1. a cigarette without a cigarette filter is 23 mm away from the smoking end; 2. the length of a cigarette filter rod is +8 mm; 3. the length of tipping paper is +3 mm. The electronic cigarette 1 atomizes tar in the electronic cigarette 1 to generate smoke without a lighting and burning process. The method and an apparatus for determining smoking termination of a conventional smoking machine cannot determine whether the electronic cigarette 1 completes smoking. When whether tobacco tar of the electronic cigarette 1 or an electric quantity of a battery runs out needs to be determined, a current conventional smoking machine cannot automatically resolve this technical problem. In the present invention, the balance 700 weighs the catcher 2 in combination with actions of the robotic arm 610. A weight change of the catcher 2 obtained by the balance 700 is transferred to the main control circuit board 300. In this method, whether smoke is still generated is determined by examining whether the weight increases. This can indirectly determine whether the tobacco tar or electric quantity runs out, thereby determining that smoking of the electronic cigarette 1 terminates.

By using the system consistent with the present invention, online successive puff analysis can be implemented, thereby substantially improving the detection efficiency. After the smoking machine automatically loads the first catcher 2, with rotation of the rotary disc 200, the smoking machine automatically smokes the electronic cigarettes 1 loaded on the smoking machine one by one. When all the electronic cigarettes 1 complete the first puffs of smoking, that is, aerosol of the first puffs of all the electronic cigarettes 1 is caught on a first catcher 2, a second catcher 2 is changed, and then the second puff of each electronic cigarette 1 is smoked. Successive puff catching analysis of the electronic cigarettes 1 may be implemented by analogy. In this way, a function may further be expanded as follows: the second puffs, the third puffs, or the like of all the electronic cigarettes 1 are sequentially caught on the first filter, the second filter, or the like. An advantage of this manner lies in that, for electronic cigarette 1 products with a same brand or specification, when quality detection needs to be performed on an entire batch of the products, quality levels vary between different individuals of a sample test batch. To reduce a detection data error caused by a produce quality difference, a quantity of tested samples must be increased. If the samples are measured one by one by using the conventional smoking machine, that is, the second cigarette is smoked after the first cigarette is completely smoked, a smoking interval of two puffs of each cigarette causes a great amount of time waste. The system provided by the present invention can fully utilize a smoking interval of each electronic cigarette 1 to complete smoking of other electronic cigarettes 1, thereby greatly improving the smoking detection efficiency. For example, a single electronic cigarette 1 is smoked for one puff every 30 seconds, and 10 minutes are consumed to complete 20 puffs of smoking. A total time of 100 minutes is consumed to complete smoking 10 cigarettes one by one. By using the present invention, each puff of smoking a single electronic cigarette 1 lasts for 3 seconds, and the rotary disc 200 rotates for 1 second. A next electronic cigarette 1 is smoked for 3 seconds, and the rotary disc 200 rotates for 1 second again. In such a manner, one puff of smoking all the 10 cigarettes can be completed in 40 seconds. A total time consumed to complete a task for all the 200 puffs of smoking all the 10 cigarettes is 13 minutes and 20 seconds, and a time of 86 minutes and 40 seconds is saved.

By using the system consistent with the present invention, the smoking machine for an electronic cigarette is combined with an automatic material changing system of a catcher. In this way, a function for which the catcher 2 is successively replenished to the smoking machine for an electronic cigarette and the catcher 2 on the smoking machine for an electronic cigarette that has completed a test is taken out and placed in a discharge store of the automatic material changing system of a catcher can be automatically implemented. Specifically, one or more smoking machines controlled by a bus are combined with the automatic material changing system of a catcher. When the main control circuit board 300 sends a detection task to each smoking machine for an electronic cigarette and the automatic material changing system of a catcher, the automatic material changing system of a catcher sends an identification instruction to the feeding identification apparatus 513 on the temporary feeding storage store 510 of each smoking machine for an electronic cigarette and receives a feedback signal indicating whether a catcher 2 exists. If no catcher 2 exists, the catcher 2 is delivered from a feeding rack of the automatic material changing system of a catcher to the temporary feeding storage store of each smoking machine for an electronic cigarette. Likewise, when one of the smoking machines for an electronic cigarette completes smoking and discharges the catcher 2 to the temporary discharge storage store 520, the discharge identification apparatus 523 of the temporary discharge storage store 520 sends the feedback signal to the automatic material changing system of a catcher. The system takes out the catcher 2 and sends it to a discharge rack of the system. Thus, in combination with 2 large capacity storage of 500 catchers and an automatic access capability of the automatic material changing system of a catcher, and a successive automatic test capability of the smoking machine for an electronic cigarette, a single successive test of large quantities of electronic cigarette samples is implemented. For example, 5 smoking machines for an electronic cigarette are combined with the automatic material changing system of a catcher. Assuming that aerosol obtained through 40 puffs of smoking each electronic cigarette is caught in a Cambridge filter catcher 2 and 400 puffs are smoked in total, generally, a quantity of puffs of consuming one electronic cigarette is less than 400. 100 spare catchers 2 are provided for each smoking machine for an electronic cigarette, so that each smoking machine for an electronic cigarette can test electronic cigarettes with 10 brands or specifications, that is, 50 samples in total. Therefore, another beneficial effect is as follows: since this process is a procedure in which the cigarette is tested one by one, that is, it takes 200 minutes to complete 400 puffs of smoking an electronic cigarette, and a next electronic cigarette is smoked. It takes about 2000 minutes in total for each of the 5 smoking machines to complete the test of 10 electronic cigarettes at the same time, approximately 33.33 hours. The entire process is automatically and continuously completed by the system, no human labor is used. Obviously, it can save a lot of labor costs and improve the utilization and working efficiency of non-working time.

As shown in FIG. 20 to FIG. 24 and FIG. 29, in this embodiment, the smoking machine for an electronic cigarette further comprises an electronic cigarette triggering system. The electronic cigarette triggering system comprises a cigarette triggering portion 3 and a triggering control cylinder 4 connected to the cigarette triggering portion 3. The cigarette triggering portion 3 is able to come into contact with the electronic cigarette 1 under control of the triggering control cylinder 4, the triggering control cylinder 4 is fixed on a connection block 5, and the connection block 5 is connected to the housing 100 by using a connection structure 6. The electronic cigarette triggering system controls the cigarette triggering portion 3 to perform an action by using the triggering control cylinder 4. When the electronic cigarette 1 needs to be powered on, the cigarette triggering portion 3 comes into contact with the electronic cigarette 1; and when the electronic cigarette 1 needs to be powered off, the cigarette triggering portion 3 hangs close to the electronic cigarette 1 and is not in contact with the electronic cigarette 1.

The electronic cigarette 1 can be clamped by using the cigarette clamp 320 of the cigarette clamping mechanism and a cigarette gripper 330. A rear portion of the electronic cigarette 1 is inserted into the housing 100 and is in communication with the smoking apparatus 440 by using a smoking channel. The triggering system is installed at a position exactly above the cigarette clamping mechanism. The triggering system controls power on and off of the electronic cigarette 1, and cooperates with a smoking action of the smoking apparatus 440, thereby implementing a function of stimulating cigarette smoking of a consumer.

Figure 21:
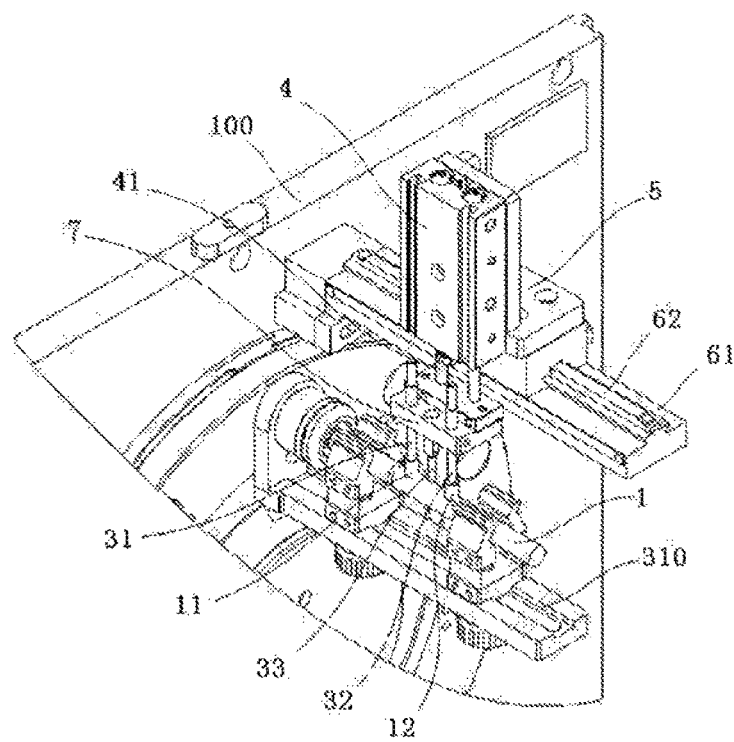
FIG. 21 is a schematic diagram when an electronic cigarette triggering system is powered on by using a direct current in a smoking machine for an electronic cigarette according to an embodiment.
Figure 22:
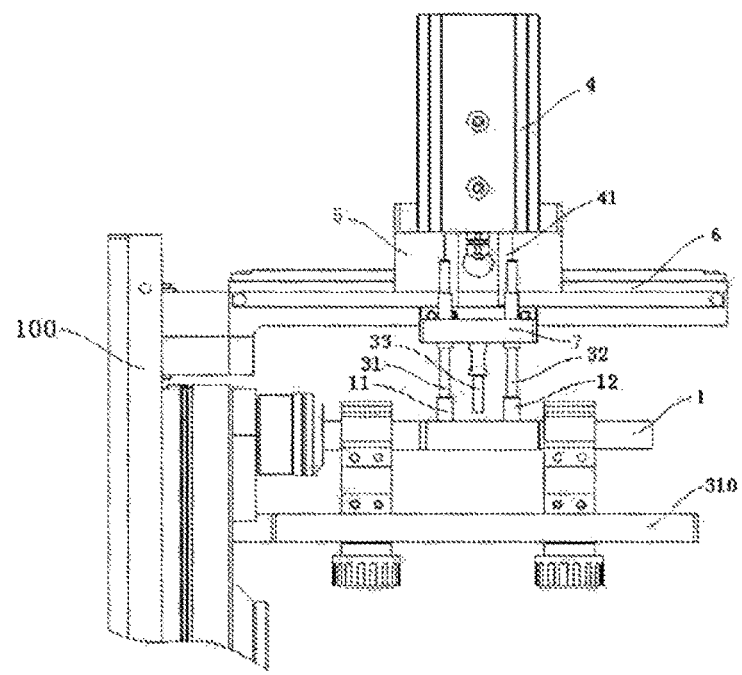
FIG. 22 is a left view of an electronic cigarette triggering system in a smoking machine for an electronic cigarette according to an embodiment.
Figure 23:
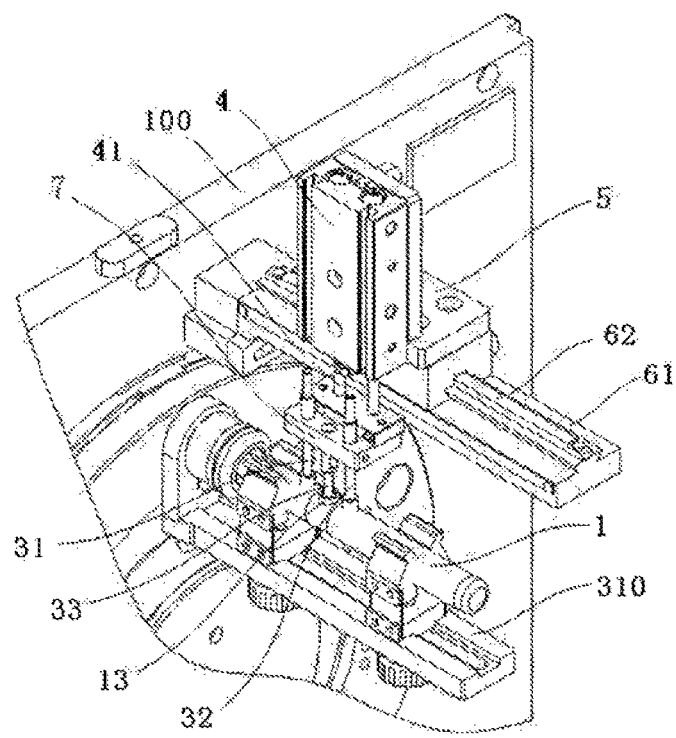
FIG. 23 is a schematic diagram when an electronic cigarette triggering system is powered on through pressing in a smoking machine for an electronic cigarette according to an embodiment.
Figure 24:
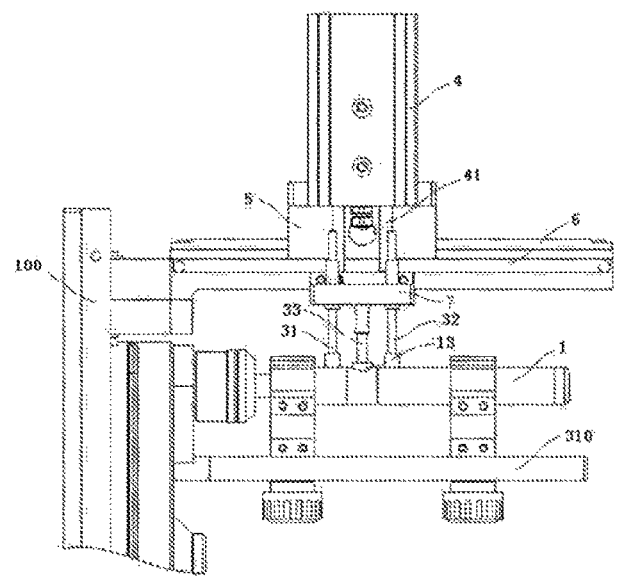
FIG. 24 is a left view of an electronic cigarette triggering system in a smoking machine for an electronic cigarette according to an embodiment.

The electronic cigarette 1 generally consists of a cigarette cartridge 201 storing tobacco tar and a cigarette rod for installing the cigarette cartridge 201, wherein the cigarette rod is provided with a battery. The battery supplies a current to a thermal resistor 2014 in the cigarette cartridge 201, and the thermal resistor 2014 is heated to atomize the tobacco tar. When the smoking machine is used to detect the electronic cigarette 1, there are two manners to power on the electronic cigarette 1. One manner is to remove an original cigarette rod with the battery of the electronic cigarette 1 and connect the cigarette cartridge 201 to a specially-made electronic cigarette rod 1001 (as shown in FIG. 25a to FIG. 27c), so that the thermal resistor 2014 in the cigarette cartridge 201 is connected to positive and negative electrodes of the electronic cigarette rod 1001 so as to form an electronic cigarette 1 for testing. In this way, a negative electrode 11 and a positive electrode 12 of the electronic cigarette 1 (that is, the electronic cigarette rod 1001) is exposed to the outside. Subsequently, this triggering system is directly connected to the negative electrode 11 and the positive electrode 12 of the electronic cigarette 1, thereby powering on the electronic cigarette 1, as shown in FIG. 21 to FIG. 22. Another manner is to perform no transformation on the original electronic cigarette 1, but to directly press a power-on button 33 on the cigarette rod of the electronic cigarette 1 in a mechanical manner, thereby powering on the electronic cigarette 1, as shown in FIG. 23 to FIG. 24.

As shown in FIG. 21 to FIG. 22, when the electronic cigarette 1 is powered on by accessing a direct current, the cigarette triggering portion 3 comprises a negative contact terminal 31 and a positive contact terminal 32. The negative contact terminal 31 corresponds to a position of the negative electrode 11 of the electronic cigarette 1, the positive contact terminal 32 corresponds to a position of the positive electrode 12 of the electronic cigarette 1, and the negative contact terminal 31 and the positive contact terminal 32 are connected to a current control apparatus. The negative contact terminal 31 and the positive contact terminal 32 are respectively in contact with the negative electrode 11 and the positive electrode 12 under control of the triggering control cylinder 4, thereby powering on the electronic cigarette 1. The current control apparatus can adjust parameters such as a current, a voltage, and power, and change the temperature of the thermal resistor 2014 in the cigarette cartridge 201, thereby adjusting an atomization degree of tobacco tar.

In the foregoing power-on manners, an external direct current has characteristics such as supplying power by using a regulated voltage and a regulated current. When a conventional smoking machine is used for testing, a one-time charging electric quantity of a rechargeable battery of the electronic cigarette is usually insufficient to completely consume tobacco tar in the cigarette cartridge 201. When a service life of the cigarette cartridge needs to be researched and examined through experiments, the examination cannot be completed in one time by using the rechargeable battery. During the examination, a sample needs to be removed to recharge the battery, which will inevitably cause an experimental process to be interrupted, resulting in an experimental error. In the foregoing technical solution, a steady direct current supplied by the current control apparatus of the smoking machine is used. Power is supplied to the cigarette cartridge 201 in a manner in which the negative contact terminal 31 and the positive contact terminal 32 are respectively in contact with the negative electrode 11 and the positive electrode 12 of the electronic cigarette 1. In such a solution, a measurement process is continuous and stable, and measurement data is accurate and effective. In addition, in the foregoing technical solution, parameters such as a voltage, a current, and power can be adjusted and set by using the current control apparatus, the temperature of a heating wire can be changed, atomization efficiency of tobacco tar under different electric quantities can be examined, and a technical basis is provided for research and development of a product.

Figure 25A:
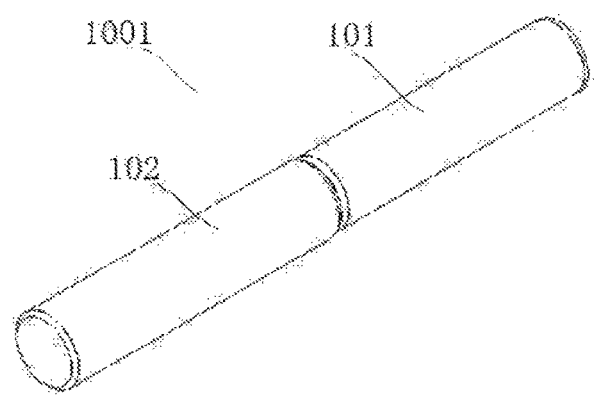
FIG. 25a to FIG. 25c are schematic structural diagrams of an electronic cigarette rod used in combination when the electronic cigarette triggering system shown in FIG. 21 is powered on by using the direct current.
Figure 25B:
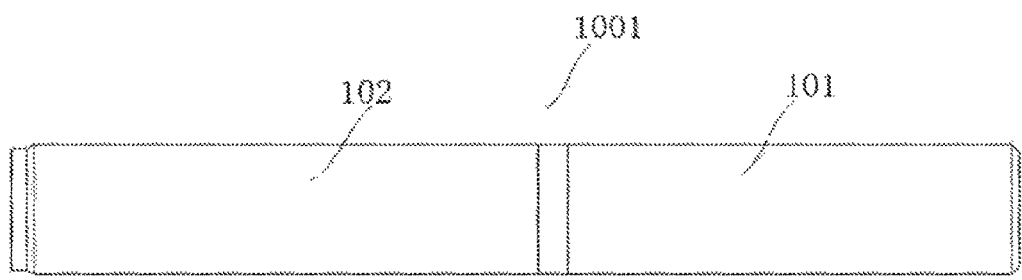
Figure 25C:
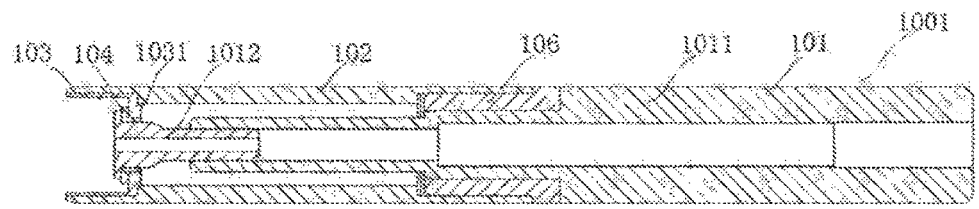

To enable the electronic cigarette 1 to be applicable to the direct-current power-on mode of the electronic cigarette triggering system, the present invention specially designs an electronic cigarette rod 1001 applicable to the electronic cigarette triggering system. an electronic cigarette 1 formed by the electronic cigarette rod 1001 provided with the cigarette cartridge 201 is applicable to the direct-current power-on mode of the electronic cigarette triggering system. A structure of the electronic cigarette rod 1001 is shown in FIG. 25a to FIG. 25c. The electronic cigarette rod 1001 comprises a positive electrode pipe 101 and a negative electrode pipe 102 sleeved over the positive electrode pipe 101. An end of the positive electrode pipe 101 far away from the cigarette cartridge 201 is in contact with the positive contact terminal 32, and an end of the positive electrode pipe 101 close to the cigarette cartridge 201 passes through the inner portion of the negative electrode pipe 102 and is in contact with a positive electrode of the cigarette cartridge 201. An outer surface of the negative electrode pipe 102 is in contact with the negative contact terminal 31, and an end of the negative electrode pipe 102 close to the cigarette cartridge 201 is in contact with a negative electrode of the cigarette cartridge 201. The negative electrode pipe 102 is isolated from the positive electrode pipe 101 by using multiple insulation rings. Since the negative electrode pipe 102 and the positive electrode pipe 101 are respectively connected to the negative electrode and the positive electrode of the cigarette cartridge 201, and are further connected to the negative contact terminal 31 and the positive contact terminal 32. In this way, the negative contact terminal 31 and the positive contact terminal 32 are respectively conductive to the negative electrode and the positive electrode of the cigarette cartridge 201. A current from the electronic cigarette triggering system causes the thermal resistor 2014 of the cigarette cartridge 201 to be heated, so that tobacco tar is atomized. In combination with a smoking action of the smoking apparatus 440, a function of stimulating cigarette smoking of a consumer is implemented.

Wherein the electronic cigarette rod 1001 may be in threaded connection to the cigarette cartridge 201 or an adapter 105. A specific structure is that a conductive threaded head 103 is fixed in the end of the negative electrode pipe 102 close to the cigarette cartridge 201, an outer surface of the threaded head 103 cooperates with an inner surface of the negative electrode pipe 102, and an inner surface of the threaded head 103 is provided with a connection thread. The cigarette cartridge 201 or the adapter 105 is provided with a thread corresponding to the thread of the inner surface of the threaded head 103, and the cigarette cartridge 201 or the adapter 105 is in threaded connection to the threaded head 103.

To ensure that a position of the positive electrode pipe 101 remains unchanged in the negative electrode pipe 102, the inner surface of the threaded head 103 is further provided with a limiting protruding ring 1031 extending radially inward. A first insulation ring 104 is filled between the limiting protruding ring 1031 and an outer surface of the positive electrode pipe 101. The positive electrode pipe 101 is fixed at a central position of the negative electrode pipe 102 by using the limiting protruding ring 1031 and the first insulation ring 104. In addition, the limiting protruding ring 1031 and the first insulation ring 104 ensure insulativity between the positive electrode pipe 101 and the negative electrode pipe 102. Meanwhile, a second insulation ring 106 is further disposed between an end of the negative electrode pipe 102 far away from the cigarette cartridge 201 and the positive electrode pipe 101. The second insulation ring 106 also ensures insulativity between the positive electrode pipe 101 and the negative electrode pipe 102.

To facilitate manufacturing and installment of the positive electrode pipe 101, the positive electrode pipe 101 comprises a positive electrode pipe rear segment 1011 and a positive electrode pipe front segment 1012. The positive electrode pipe front segment 1012 is inserted into the positive electrode pipe rear segment 1011. An outer surface of the positive electrode pipe rear segment 1011 is in contact with the positive contact terminal 32, and the positive electrode pipe front segment 1012 is in contact with the positive electrode of the cigarette cartridge 201. The middle of the positive electrode pipe 101 is provided with a smoking channel 97 in communication with a smoking channel 111 of the cigarette cartridge 201. After the cigarette cartridge 201 is installed on the electronic cigarette rod 1001, two ends of the smoking channel 97 of the positive electrode pipe 101 are respectively in communication with the smoking channel 111 of the cigarette cartridge 1 in external air, and the smoking channel 111 of the cigarette cartridge 1 is in communication with the smoking apparatus 440 located inside the smoking machine.

Figure 26A:
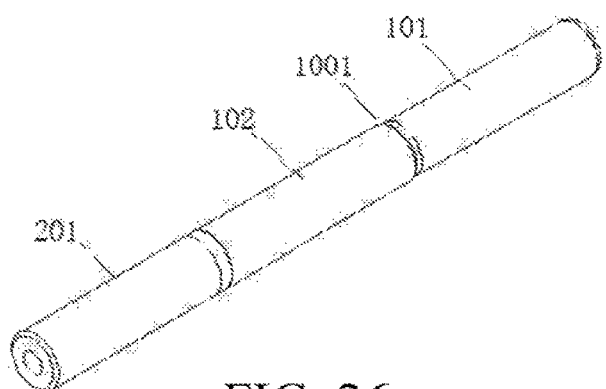
FIG. 26a to FIG. 26c are schematic structural diagrams of the electronic cigarette rod shown in FIG. 25a to FIG. 25c directly connected to a cigarette cartridge.
Figure 26B:
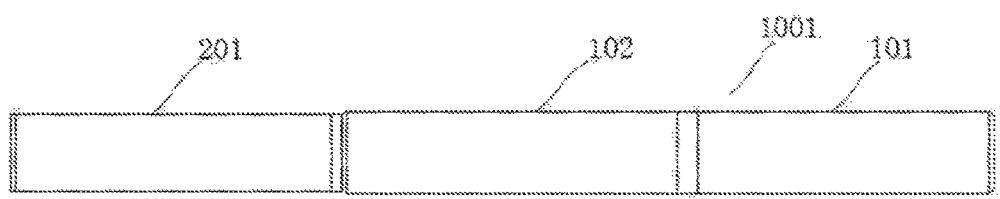
Figure 26C:
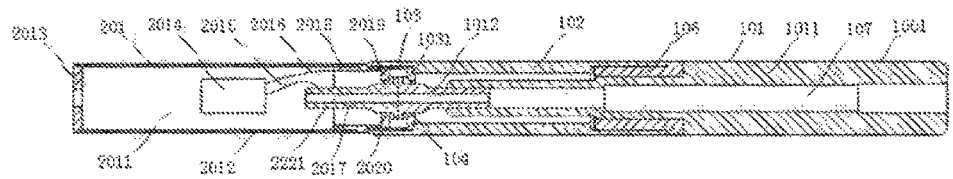
Figure 27A:
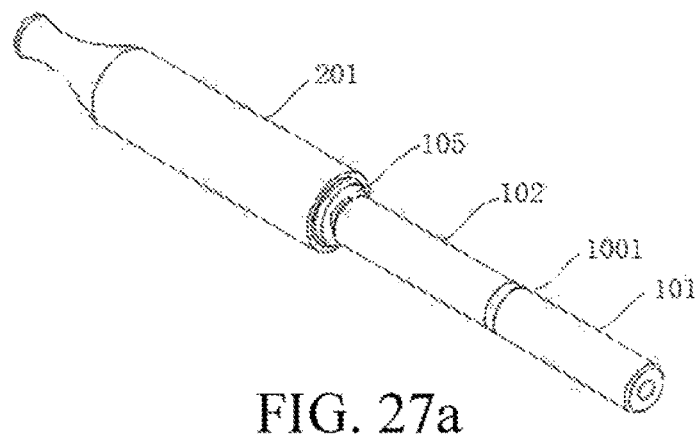
FIG. 27a to FIG. 27c are schematic structural diagrams of the electronic cigarette rod shown in FIG. 25a to FIG. 25c connected to a cigarette cartridge by using an adapter.
Figure 27B:
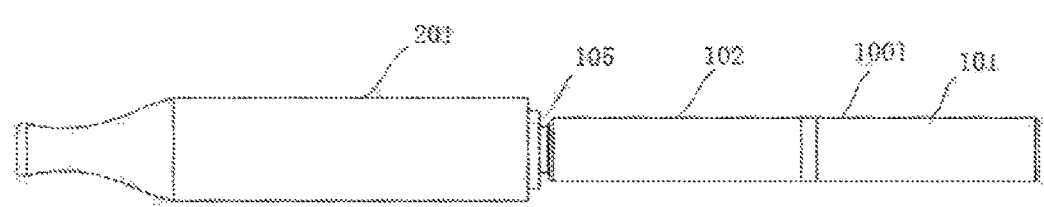
Figure 27C:
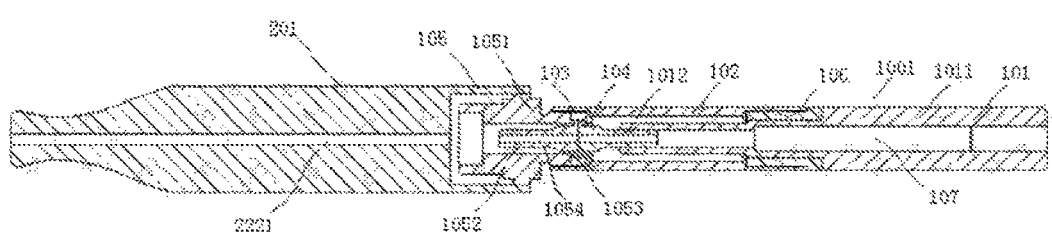
Figure 28:
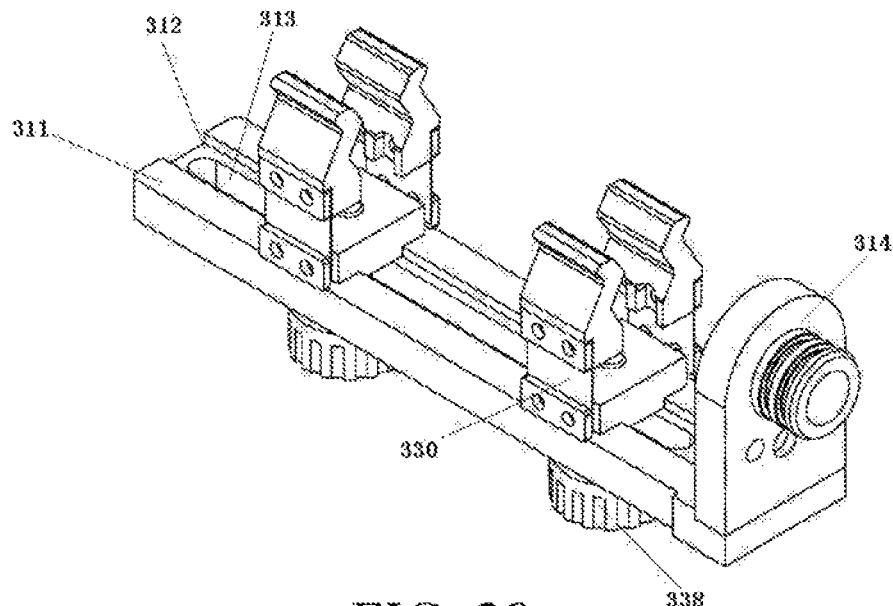
FIG. 28 is a schematic structural diagram when a cigarette clamping mechanism is not provided with a cigarette clamp in a smoking machine for an electronic cigarette according to an embodiment.
Figure 29:
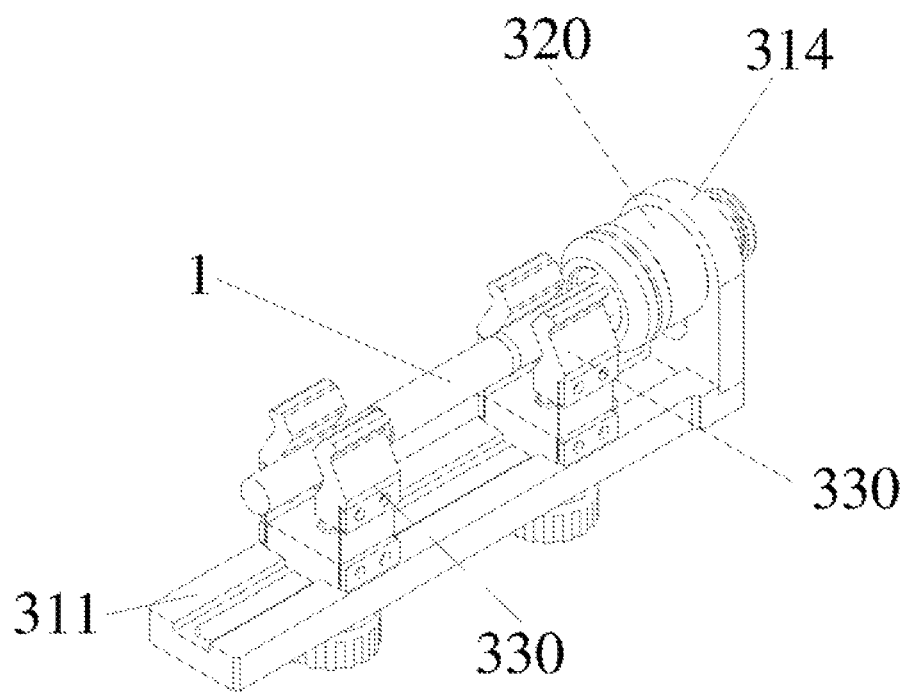
FIG. 29 is a schematic structural diagram when a cigarette clamping mechanism is in use in a smoking machine for an electronic cigarette according to an embodiment.
Figure 30:
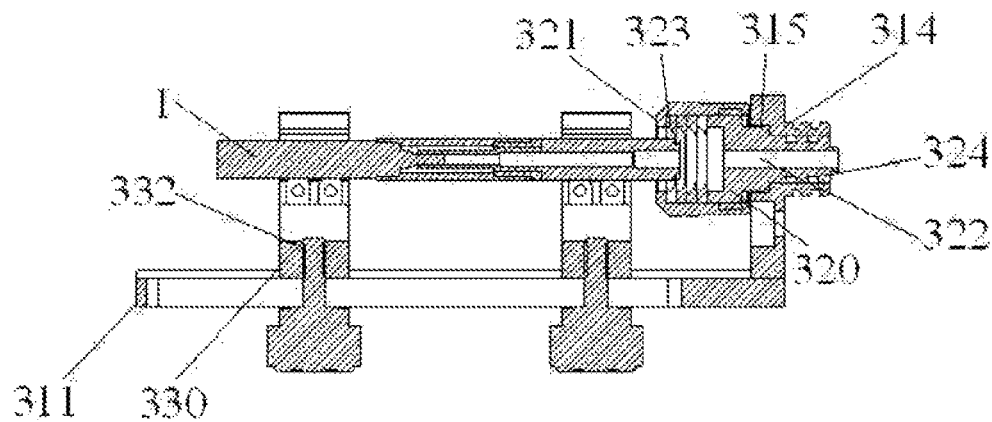
FIG. 30 is a schematic cross-sectional structural diagram of FIG. 29.
Figure 31:
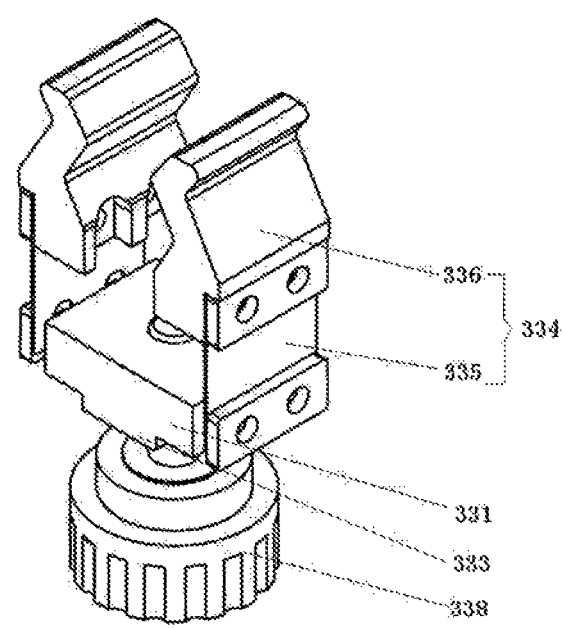
FIG. 31 is a schematic structural diagram of a cigarette gripper of a cigarette clamping mechanism in a smoking machine for an electronic cigarette according to an embodiment.

The electronic cigarette rod 1001 may be directly connected to the cigarette cartridge 1 (as shown in FIG. 26a to FIG. 26c), or may be connected to the cigarette cartridge 1 by using the adapter 105 (as shown in FIG. 27a to FIG. 27c).

As shown in FIG. 26a to FIG. 26c, the electronic cigarette rod 1001 is directly in threaded connection to the cigarette cartridge 1. The cigarette cartridge 201 comprises an atomization cavity 2011 formed by an electronic cigarette pipe 2012 and an electronic cigarette cap 2013. The thermal resistor 2014 is disposed inside the atomization cavity 2011. The thermal resistor 2014 is connected to a negative conductive pipe 2018 by using a negative wiring 2016, and the thermal resistor 2014 is further connected to a positive conductive pipe 2017 by using a positive wiring 2015. The positive conductive pipe 2017 is located inside the negative conductive pipe 2018. The negative conductive pipe 2018 is in threaded connection to the threaded head 103 of the electronic cigarette rod 1001. The positive conductive pipe 2017 is in contact with the positive electrode pipe 101 of the electronic cigarette rod 1001. To ensure that the positive conductive pipe 2017 is located at a central position and to ensure an insulation effect between the positive conductive pipe 2017 and the negative conductive pipe 2018, the negative conductive pipe 2018 is provided with a positioning protruding ring 2019 radially protruding inward. A third insulation ring 2020 is disposed between the positioning protruding ring 2019 and the positive conductive pipe 2017.

After the cigarette cartridge 201 is installed on the electronic cigarette rod 1001, the two ends of the smoking channel 97 of the positive electrode pipe 101 are respectively in communication with the smoking channel 111 of the cigarette cartridge 1 in external air, and the smoking channel 111 of the cigarette cartridge 1 extends into the atomization cavity 2011 of the cigarette cartridge 1. The atomization cavity 2011 is in communication with the smoking apparatus 440 located inside the smoking machine by using a through hole on the electronic cigarette cap 2013.

As shown in FIG. 27a to FIG. 27c, the electronic cigarette rod 1001 is connected to the cigarette cartridge 201 by using the adapter 105. The electronic cigarette rod 1001 further comprises the adapter 105. The adapter 105 comprises a negative connection pipe 1051 and a positive connection pipe 1052 located inside the negative connection pipe 1051. Two ends of the negative connection pipe 1051 are respectively in contact with the negative electrode pipe 102 and the negative electrode of the cigarette cartridge 201. Two ends of the positive connection pipe 1052 are respectively in contact with the positive electrode pipe 101 and the positive electrode of the cigarette cartridge 201.

To ensure that the positive connection pipe 1052 is located at a central position and to ensure an insulation effect between the positive connection pipe 1052 and the negative connection pipe 1051, a fourth insulation ring 953 is disposed between the negative connection pipe 1051 and the positive connection pipe 1052. The middle of the adapter 105 is further provided with a smoking channel 954 passing through the positive connection pipe 1052. The smoking channel 97 of the electronic cigarette rod 1001 is in communication with the smoking channel 111 of the cigarette cartridge 201 by using the smoking channel 954.

A peripheral surface of the negative connection pipe 1051 is provided with a thread. One end of the negative connection pipe 1051 is in threaded connection to the threaded head 103 of the electronic cigarette rod 1001, and the other end is in threaded connection to the cigarette cartridge 201. The diameter of the peripheral surface of the negative connection pipe 1051 cooperating with the threaded head 103 and the cigarette cartridge 201 depends on the diameter of a threaded cooperating surface of the threaded head 103 and the cigarette cartridge 201. The cigarette cartridges 201 with different diameters may be connected to the electronic cigarette rod 1001 by using the adapter 105, thereby expanding an applicable range of the electronic cigarette rod 1001.

As shown in FIG. 23 to FIG. 24, the cigarette triggering portion 3 comprises a cigarette pressing terminal 13, and the cigarette pressing terminal 13 corresponds to a position of the power-on button 33 of the electronic cigarette 1. The triggering control cylinder 4 controls the cigarette pressing terminal 13 to press the power-on button 33 of the electronic cigarette 1, thereby powering on the electronic cigarette 1.

A pressing force of the cigarette pressing terminal 13 may be adjusted. A reducing valve is disposed on the triggering control cylinder 4. Air source pressure of the triggering control cylinder 4 is adjustable by adjusting the reducing valve, thereby controlling the pressure of the cigarette pressing terminal 13, and the cigarette pressing terminal 13 is able to be adaptive to pressing strength required by electronic cigarettes 1 with different versions.

The foregoing solution is used to trigger the electronic cigarette 1, and a pre-triggering time may be set pinpointing to a millisecond level. When the smoking machine periodically works based on a standard smoking time and a smoking interval, time needs to be controlled quite accurately. A pressing action and an electronic cigarette triggering moment itself will lead to a triggering delay. In the foregoing technical solution, an advance amount of a given triggering time may be implemented, thereby eliminating a delay problem of the triggering time.

The foregoing cigarette triggering portion 3 is fixed on an integrated block 7. The integrated block 7 is fixedly connected to the piston rod 41 of the triggering control cylinder 4. The integrated block 7 and the cigarette triggering portion 3 are driven to move by triggering scalability of the piston rod 41 of the triggering control cylinder 4, so that a position of the cigarette triggering portion 3 is adjusted and contact between the cigarette triggering portion 3 and the electronic cigarette 1 is controlled. To more conveniently adjust relative positions of the cigarette triggering portion 3 and the electronic cigarette 1, an axis of the piston rod 41 of the triggering control cylinder 4 is preferably disposed perpendicular to an axis of the electronic cigarette 1.

The negative contact terminal 31 and the positive contact terminal 32 of the cigarette triggering portion 3 used for direct current power-on and the cigarette pressing terminal 13 used for pressing power-on may be jointly integrated and installed on one integrated block 7. In this way, the cigarette triggering portion 3 has two triggering manners and the cigarette triggering portion 3 may flexibly select direct current power-on or pressing power-on. Wherein, a preferable arranging manner is as follows: the cigarette pressing terminal 13 is located between the negative contact terminal 31 and the positive contact terminal 32, and the three terminals are sequentially arranged in a direction parallel to the axis of the electronic cigarette 1.

As shown in FIG. 20 to FIG. 24, the connection structure 6 comprises a fixed rod 61 connected to the smoking machine. The fixed rod 61 is provided with a guiding rail 62, and a connection block 5 slides on the guiding rail 62. A position of the cigarette triggering portion 3 may be flexibly adjusted when the connection block 5 slides on the guiding rail 62, so that the cigarette triggering portion 3 may be applicable to electronic cigarettes 1 with different specifications. To more conveniently adjust the relative position of the cigarette triggering portion 3, an axis of the guiding rail 62 is parallel to the axis of the electronic cigarette 1. The connection block 5 is further provided with a lock bolt. After the connection block 5 slides in position, the lock bolt is pressed on the guiding rail 62, so that the connection block 5 is fixed relative to the guiding rail 62.

A position of the cigarette triggering portion 3 in a direction parallel to the axis of the electronic cigarette 1 is adjusted through the sliding of the connection block 5 on the guiding rail 62; and a position of the cigarette triggering portion 3 in a direction perpendicular to the axis of the electronic cigarette 1 is adjusted through stretching of the piston rod 41 of the triggering control cylinder 4. In combination of the two adjustment manners, the cigarette triggering portion 3 may be adjusted to different positions. The triggering system can be applicable to electronic cigarettes 1 with different specifications.

In conclusion, for the electronic cigarette triggering system consistent with the present invention and the electronic cigarette rod used in combination, automatic control of power-on of the electronic cigarette is implemented by installing a specialized electronic cigarette triggering system on the smoking machine. This resolves a problem that an existing smoking machine has no electronic cigarette triggering system. In addition, in use of the triggering system, a triggering time of the electronic cigarette is accurately controlled, and parameters such as a current value and an on duration of the electronic cigarette may be adjusted based on an experimental requirement. Therefore, the present invention effectively overcomes various disadvantages in the prior art and has a high industrial usage value.

As shown in FIG. 28 to FIG. 31, the clamping mechanism body 310 comprises a horizontal base plate 311 and a vertical supporting plate 314, an upper surface of the horizontal base plate 311 is provided with a guiding groove 312, the guiding groove 312 is disposed in a direction of the length of the horizontal base plate 311; and a bottom portion of the vertical supporting plate 314 is connected to a rear end of the horizontal base plate 311, and the vertical supporting plate 314 is provided with a base through hole 315 penetrating in a horizontal direction; the other end of the cigarette clamp 320 is a disc body connection end 324, and the disc body connection end 324 passes through the base through hole 315 of the vertical supporting plate 314; and the cigarette clamping mechanism further comprises a cigarette gripper 330, and the cigarette gripper 330 comprises a gripper base plate 331 and two side surface clamping portions 334 disposed opposite to each other provided on the gripper base plate 331, the gripper base plate 331 is installed on the guiding groove 312 of the horizontal base plate 311 and is movable in a direction of the length of the guiding groove 312, and the two side surface clamping portions 334 are symmetrically disposed by using a vertical plane of a central axis of the axial through hole 322 as a central axial plane.

The smoking end of a cigarette is inserted into the cigarette clamping end 321 of the cigarette clamp 320. The two side surface clamping portions 334 are symmetrically disposed by using a vertical plane of a central axis of the axial through hole 322 as a central axial plane, so that after the two side surface clamping portions 334 disposed opposite to each other clamp side surfaces of the cigarette, a central axis of the cigarette can accurately align with the axial through hole 322 on the cigarette clamp 320, keeping the cigarette airtight all the time after being inserted into the cigarette clamp 320 and keeping a position of the cigarette to be stable. In addition, the gripper base plate 331 is movable in the direction of the length of the guiding groove 312, so that a position at which the two side surface clamping portions 334 clamp the cigarette can change based on a structure of the cigarette. This enables the cigarette clamping mechanism consistent with the present invention to clamp cigarettes of various types.

The rotary disc 200 consistent with the present invention is perpendicular to a horizontal plane, and the electronic cigarette 1 circumferentially rotates along with the rotary disc 200 in a smoking experiment process, so that tobacco tar in a cigarette cartridge flows and fully immerses the oil guiding cotton, thus ensuring sufficient and steady supply of the tobacco tar to an atomizer, and guaranteeing atomization efficiency, atomization amount, and the stability and accuracy of experiment data. The cigarette clamping mechanism cooperates with a rotation direction of the rotary disc 200 to stably clamp the electronic cigarette 1. The automatic loading and weighing system of a catcher cooperates with an operation direction of the rotary disc 200 to control the catcher 2 to move to a required position. In addition, a ventilation direction of the catcher 2 is always consistent with a smoking experiment direction of the electronic cigarette 1. This can ensure that the catcher 2 is quickly and stably changed during a smoking interval of two puffs, and can also ensure that the catcher 2 returns to the smoking position after a weighing action is completed during the smoking interval of two puffs. The electronic cigarette triggering system consistent with the present invention implements automatic control of triggering of the electronic cigarette 1 and resolves a problem that an existing smoking machine does not have a manually triggered electronic cigarette triggering system and external power supply.

The two side surface clamping portions 334 are symmetrically disposed by using a vertical plane of a central axis of the axial through hole 322 as a central axial plane, so that after the two side surface clamping portions 334 clamp side surfaces of the cigarette, a central axis of the cigarette can accurately align with the axial through hole 322 on the cigarette clamp 320, keeping the cigarette airtight all the time after being inserted into the cigarette clamp 320 and keeping a position of the cigarette to be stable. In addition, the gripper base plate 331 is movable in a direction of the length of the guiding groove 312, so that a position at which the two side surface clamping portions 334 clamp the cigarette can change based on a structure of the cigarette. This enables the cigarette clamping mechanism consistent with the present invention to clamp cigarettes of various types.

To prevent the gripper base plate 331 moving to a corresponding clamping position from sliding freely, a bottom surface of the guiding groove 312 is provided with a guiding through hole 313. The gripper base plate 331 is provided with a fastening hole 332. A fastening member 338 sequentially passes through the guiding through hole 313 and the fastening hole 332 so as to connect the horizontal base plate 311 and the gripper base plate 331. In an embodiment, the fastening hole 332 is a threaded hole and the fastening member 338 is a screw. This structure enables the gripper base plate 331 to be fixedly connected to the horizontal base plate 311 after the gripper base plate 331 moves to a required position in a direction of the length of the guiding groove 312, so that a position of the gripper base plate 331 can be fixed.

After the gripper base plate 331 is fixedly connected to the horizontal base plate 311, the gripper base plate 331 may move from left to right or the other way around. Therefore, a bottom surface of the gripper base plate 331 is provided with a protruding portion 333. The protruding portion 333 is inserted into the guiding groove 312 and is in contact with the bottom surface of the guiding groove 312. The fastening hole 332 passes through the protruding portion 333. This structure enables the protruding portion 333 to be positioned in the guiding groove 312, and effectively prevents the gripper base plate 331 from moving from left to right or the other way around, so that a position of the cigarette remains stable. The gripper base plate 331 and the protruding portion 333 are integrally formed to form a T-shaped structure. The protruding portion 333 is in contact with the bottom surface of the guiding groove 312, and the gripper base plate 331 is in contact with an upper surface of the horizontal base plate 311.

To facilitate a cigarette to be installed between the two side surface clamping portions 334, each side surface clamping portion 334 comprises a spring plate 335 disposed on the gripper base plate 331 and a guiding member 336 disposed in an inner side of the spring plate 335. An inner side surface of the guiding member 336 is provided with a V-shaped groove. V-shaped grooves of two guiding members 336 on a same gripper base plate 331 are disposed opposite to each other. The spring plate 335 is elastic. When the two spring plates 335 are pulled open, a cigarette can be conveniently placed between the two spring plates 335, a resilience of the two spring plates 335 can be used to clamp the cigarette, and the two spring plates 335 can clamp cigarettes with different sizes. A cigarette may be clamped between V-shaped grooves on inner side surfaces of the two guiding members 336, so that the cigarette is in contact with each V-shaped groove through two points. This enables the V-shaped grooves to more stably clamp and fix the cigarette.

A connected line between central points of groove bottoms of the V-shaped grooves of the two guiding members 336 is perpendicular to the central axis of the axial through hole 322 on the cigarette clamp 320. This structure enables a central axis of a cigarette clamped by the two V-shaped grooves to accurately align with the central axis of the axial through hole 322.

An inner wall of the cigarette clamping end 321 of the cigarette clamp 320 is provided with a labyrinth ring 323. This structure facilitates the smoking end of the cigarette to be connected to the cigarette clamping end 321 of the cigarette clamp 320.

There are at least two cigarette grippers 330. At least two cigarette grippers 330 can clamp a cigarette at multiple clamping positions. This ensures a stable position for each cigarette.

To restrict a position of the cigarette clamp 320 installed on the base through hole 315 of the vertical supporting plate 314, an outer diameter of the cigarette clamping end 321 of the cigarette clamp 320 is greater than a diameter of the base through hole 315 of the vertical supporting plate 314.

Generally, the electronic cigarette 1 has a weight far greater than a conventional cigarette. The electronic cigarette 1 loaded on the smoking machine can maintain at an accurate and stable position by using the cigarette clamping mechanism. In addition, the mechanism adapts to most cylindrical electronic cigarettes 1 with different diameters, and the cigarette gripper 330 may be changed to adapt to an electronic cigarette 1 in a special shape. It is convenient to replace the cigarette gripper 330 and the clamping mechanism, and the electronic cigarette 1 can be conveniently loaded and removed.

In conclusion, the present invention effectively overcomes various disadvantages in the prior art and has high industrial usage value.

The foregoing embodiments merely exemplarily describe the principle and effect of the present invention, and are not intended to limit the present invention. Any person skilled in the art can make modifications or changes to the foregoing embodiments without departing from the spirit and scope of the present invention. Therefore, all equivalent modifications or changes made by those of ordinary skill in the art without departing from the spirit and technical idea disclosed in the present invention shall still be covered by the claims of the present invention.

What is claimed is:

1. A smoking machine for an electronic cigarette, comprising: a housing (100); a rotary disc (200) installed on the housing (100), the rotary disc (200) rotates relative to the housing (100) with a central axis of the rotary disc as a center; at least one disc-body smoking through hole (210) is disposed on an end face of the rotary disc (200); a housing sealing member (120) is disposed on the housing (100), a sealing ventilation hole (121) penetrating into an inner portion of the housing (100) is provided in the housing sealing member (120), and when the sealing ventilation hole (121) is in communication with one end of a catcher (2), the other end of the catcher (2) is in communication with a smoking apparatus (440);

wherein the central axis of the rotary disc (200) is parallel to a horizontal plane; and the smoking machine for an electronic cigarette comprising at least one cigarette clamping mechanism, the cigarette clamping mechanism comprising a clamping mechanism body (310) and a cigarette clamp (320) disposed on the clamping mechanism body (310), wherein the cigarette clamp (320) is installed on the disc-body smoking through hole (210) of the rotary disc (200); one end of the cigarette clamp (320) is a cigarette clamping end (321) for inserting therein an electronic cigarette (1) in a horizontal direction, the cigarette clamp (320) is provided with an axial through hole (322) penetrating in a horizontal direction for smoke to pass through, and the rotary disc (200) is able to rotate to a position to make the axial through hole (322) in communication with the sealing ventilation hole (121) of the housing sealing member (120).

2. The smoking machine for an electronic cigarette as in claim 1, wherein when two or more disc-body smoking through holes (210) exist, the two or more disc-body smoking through holes (210) are evenly arranged on the rotary disc (200), and distances between central axes of the disc-body smoking through holes (210) and the central axis of the rotary disc (200) are the same.

3. The smoking machine for an electronic cigarette as in claim 2, wherein the housing sealing member (120) is disposed on an upper portion of a side surface of the housing (100), a central axis of the sealing ventilation hole (121) and the central axis of the rotary disc (200) both pass through a vertical plane perpendicular to the horizontal plane.

4. The smoking machine for an electronic cigarette as in claim 1, wherein an end face of the housing sealing member (120) is in contact with the end face of the rotary disc (200), and the end face of the rotary disc (200) in contact with the housing sealing member (120) is a plane.

5. The smoking machine for an electronic cigarette as in claim 1, wherein further comprising an automatic loading and weighing system of a catcher, the automatic loading and weighing system of a catcher comprises:

a temporary feeding storage store (510) and a temporary discharge storage store (520), which are disposed on the housing (100) of the smoking machine for an electronic cigarette and in communication with an inner portion of the housing (100);

a transmission mechanism (600), a balance (700), an ejector pin assembly (400), and a discharge transferring mechanism (800), which are disposed inside the housing (100); and a main control circuit board (300) electrically connected to the ejector pin assembly (400), the transmission mechanism (600), the temporary feeding storage store (510), the temporary discharge storage store (520), and the discharge transferring mechanism (800);

the temporary feeding storage store (510) receives the catcher (2) disposed from an outer portion of the smoking machine for an electronic cigarette, and the catcher (2) is taken out from the temporary discharge storage store (520);

a robotic arm (610) is installed on the transmission mechanism (600), the robotic arm (610) obtains the catcher (2), the transmission mechanism (600) drives the robotic arm (610) to move, so that the catcher (2) reaches a preparation position and a weighing position, and during moving of the catcher (2), a central axis of the catcher (2) remains in parallel to a central axis of the sealing ventilation hole (121);

the balance (700) weighs the catcher (2) reaching the weighing position;

the ejector pin assembly (400) pushes the catcher (2) to horizontally move to a smoking position, and the ejector pin assembly (400) is provided with a vapor channel (421) for sucking vapor; and the discharge transferring mechanism (800) transfers the catcher (2) to the temporary discharge storage store (520).

6. The smoking machine for an electronic cigarette as in claim 5, wherein the discharge transferring mechanism (800) comprises an inclined slideway (810) for the catcher (2) to slide and a discharge pushing cylinder (820), a horizontal height of an end of the inclined slideway (810) close to the temporary discharge storage store (520) is less than a horizontal height of an end of the inclined slideway (810) far away from the temporary discharge storage store (520), the discharge pushing cylinder (820) is disposed below the end of the inclined slideway (810) close to the temporary discharge storage store (520), and a piston rod of the discharge pushing cylinder (820) is located exactly below the temporary discharge storage store (520).

7. The smoking machine for an electronic cigarette as in claim 5, wherein the catcher (2) comprises a catching body (21) and a vapor guiding head (22) disposed on each of two axial end faces of the catching body (21); the robotic arm (610) is formed by two grippers (611) with a V-shaped groove at an end portion; and the V-shaped groove supports the corresponding vapor guiding head (22).

8. The smoking machine for an electronic cigarette as in claim 5, wherein the ejector pin assembly (400) comprises an ejector pin cylinder (410) and an adapter sealing member (420), the adapter sealing member (420) is connected to a piston rod of the ejector pin cylinder (410), the vapor channel (421) is disposed on the adapter sealing member (420), and when the catcher (2) is located at the smoking position, the adapter sealing member (420) is in sealing connection to a vapor outlet end of the catcher (2), and the vapor channel (421) communicates the catcher (2) with the smoking apparatus (440).

9. The smoking machine for an electronic cigarette as in claim 1, wherein further comprising an electronic cigarette triggering system, the electronic cigarette triggering system comprises a cigarette triggering portion (3) and a triggering control cylinder (4) connected to the cigarette triggering portion (3), the cigarette triggering portion (3) is able to come into contact with the electronic cigarette (1) under control of the triggering control cylinder (4), the triggering control cylinder (4) is fixed on a connection block (5), and the connection block (5) is connected to the housing (100) by using a connection structure (6).

10. The smoking machine for an electronic cigarette as in claim 9, wherein the cigarette triggering portion (3) comprises a negative contact terminal (31) and a positive contact terminal (32), the negative contact terminal (31) corresponds to a position of a negative electrode (11) of the electronic cigarette (1), the positive contact terminal (32) corresponds to a position of a positive electrode (12) of the electronic cigarette (1), and the negative contact terminal (31) and the positive contact terminal (32) are connected to a current control apparatus.

11. The smoking machine for an electronic cigarette as in claim 9, wherein the cigarette triggering portion (3) comprises a cigarette pressing terminal (33), and the cigarette pressing terminal (33) corresponds to a position of a power-on button (13) of the electronic cigarette (1).

12. The smoking machine for an electronic cigarette as in claim 1, wherein the clamping mechanism body (310) comprises a horizontal base plate (311) and a vertical supporting plate (314), an upper surface of the horizontal base plate (311) is provided with a guiding groove (312), the guiding groove (312) is disposed in a direction of the length of the horizontal base plate (311); and a bottom portion of the vertical supporting plate (314) is connected to a rear end of the horizontal base plate (311), and the vertical supporting plate (314) is provided with a base through hole (315) penetrating in a horizontal direction;

the other end of the cigarette clamp (320) is a disc body connection end (324), and the disc body connection end (324) penetrates into the base through hole (315) of the vertical supporting plate (314); and the cigarette clamping mechanism further comprises a cigarette gripper (330), and the cigarette gripper (330) comprises a gripper base plate (331) and two side surface clamping portions (334) disposed opposite to each other provided on the gripper base plate (331), the gripper base plate (331) is installed on the guiding groove (312) of the horizontal base plate (311) and is movable in a direction of the length of the guiding groove (312), and the two side surface clamping portions (334) are symmetrically disposed by using a vertical plane of a central axis of the axial through hole (322) as a central axial plane.

* * * * *